United States Patent [19]

Turner et al.

[11] Patent Number: 4,765,338

[45] Date of Patent: Aug. 23, 1988

[54] REUSEABLE HEAT TRANSFER DEVICES FOR THE SCALP

[76] Inventors: Richard W. Turner, 3610 Calle Colina Roca, Alpine, Calif. 92001; Vernon E. Stewart, 318 S. 4th St., Moberly, Mo. 65270

[21] Appl. No.: 454,413

[22] Filed: Dec. 29, 1982

[51] Int. Cl.[4] .............................................. A61F 7/00
[52] U.S. Cl. ..................................................... 128/402
[58] Field of Search .................. 128/24.1, 68.1, 76 R, 128/82.1, 97, 163, 380, 399, 402; 2/171.1, 171.2, 181.4

[56] References Cited

U.S. PATENT DOCUMENTS

| | | | |
|---|---|---|---|
| 1,542,000 | 6/1925 | Parsons | 2/171.1 |
| 2,049,723 | 8/1936 | Pomeranz | 128/402 |
| 3,776,244 | 12/1973 | Morgan | 2/171.2 |
| 3,820,780 | 6/1974 | Tarbox | 128/97 |
| 4,055,188 | 10/1977 | Pelton | 128/402 |
| 4,131,953 | 1/1979 | Kimotsuki | 2/171.1 |
| 4,382,446 | 5/1983 | Truelock et al. | 128/402 |

*Primary Examiner*—Max Hindenburg
*Attorney, Agent, or Firm*—Thomas M. Scofield

[57] ABSTRACT

Improvements in reuseable, heat exchanging head pieces for cooling or heating substantially the entire hair bearing (scalp) area of the human head; improvements in a blank form for use in the manufacture of such product for the said purposes for filling with reuseable heat exchanging materials; a reuseable, heat exchanging head piece employable with cancer chemotherapy patients in order to cool the scalp zone of the head in order to prevent hair loss during chemotherapy treatment and injections; improved reuseable devices and processes for heat exchanging the human scalp, including such with a variable or adjustable size headband constriction and limited, yet controllable upper head surface of skull surface compression for full, substantially "holiday" free cooling or heating; further improvements in such heat exchanging head pieces wherein the blank form and heat exchanging head pieces are alternatively used or available for use in a one-shot or nonreuseable configuration.

4 Claims, 7 Drawing Sheets

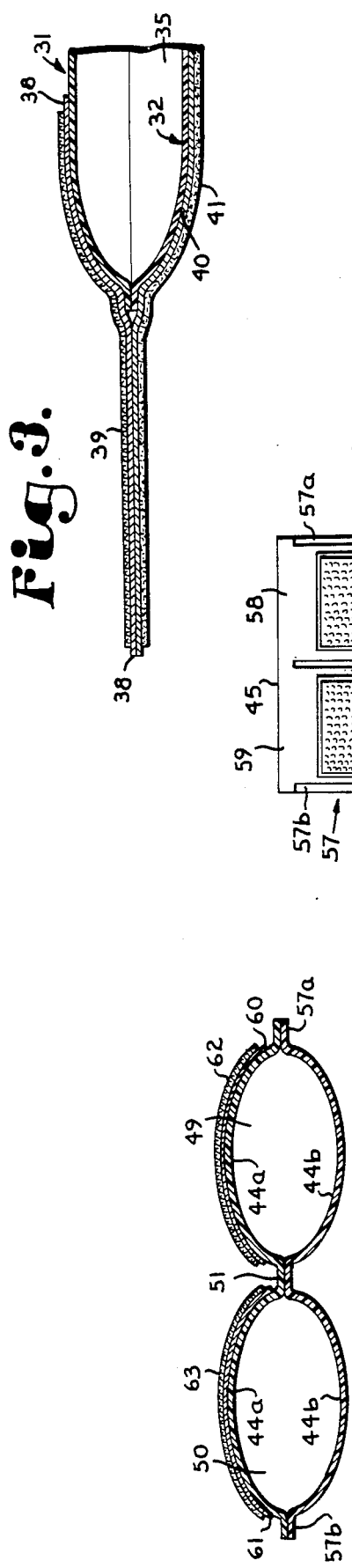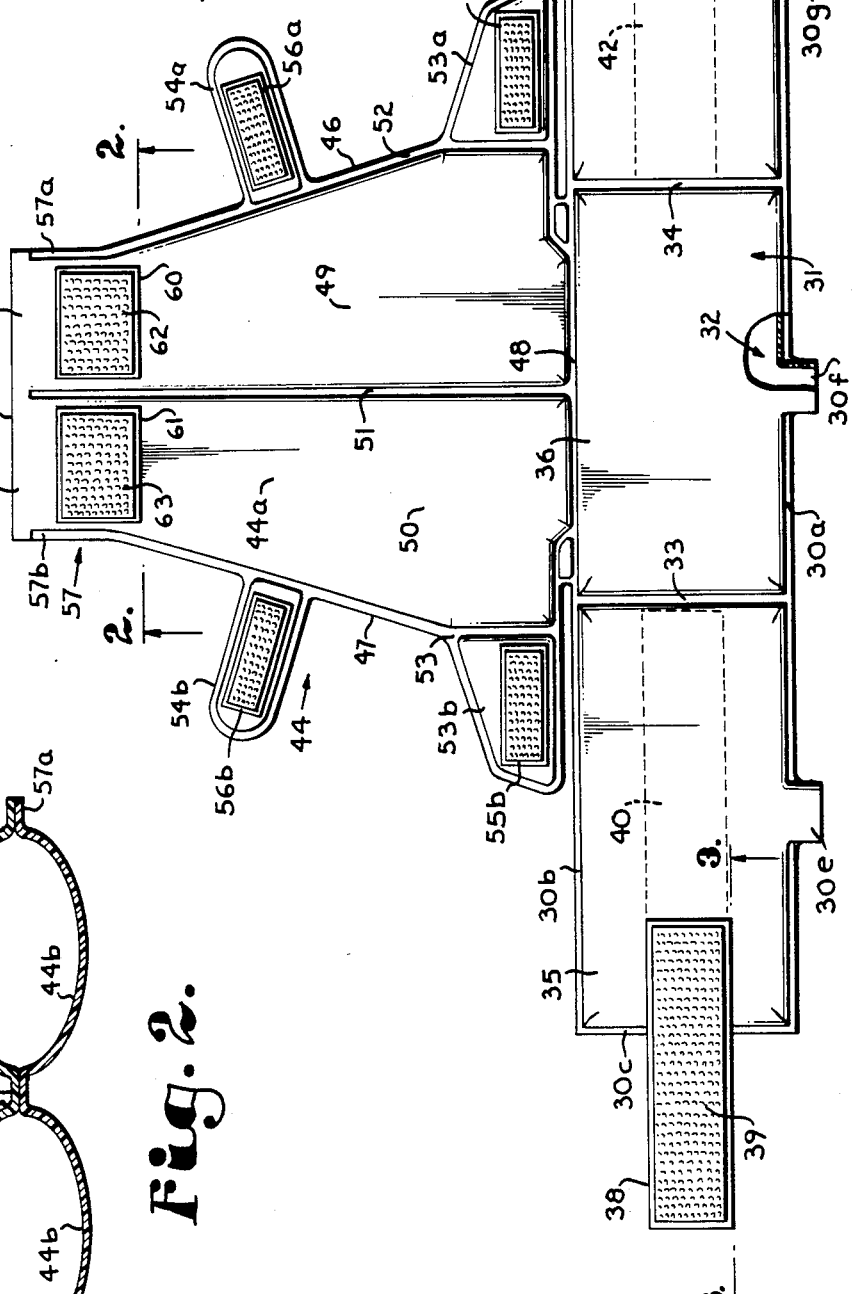

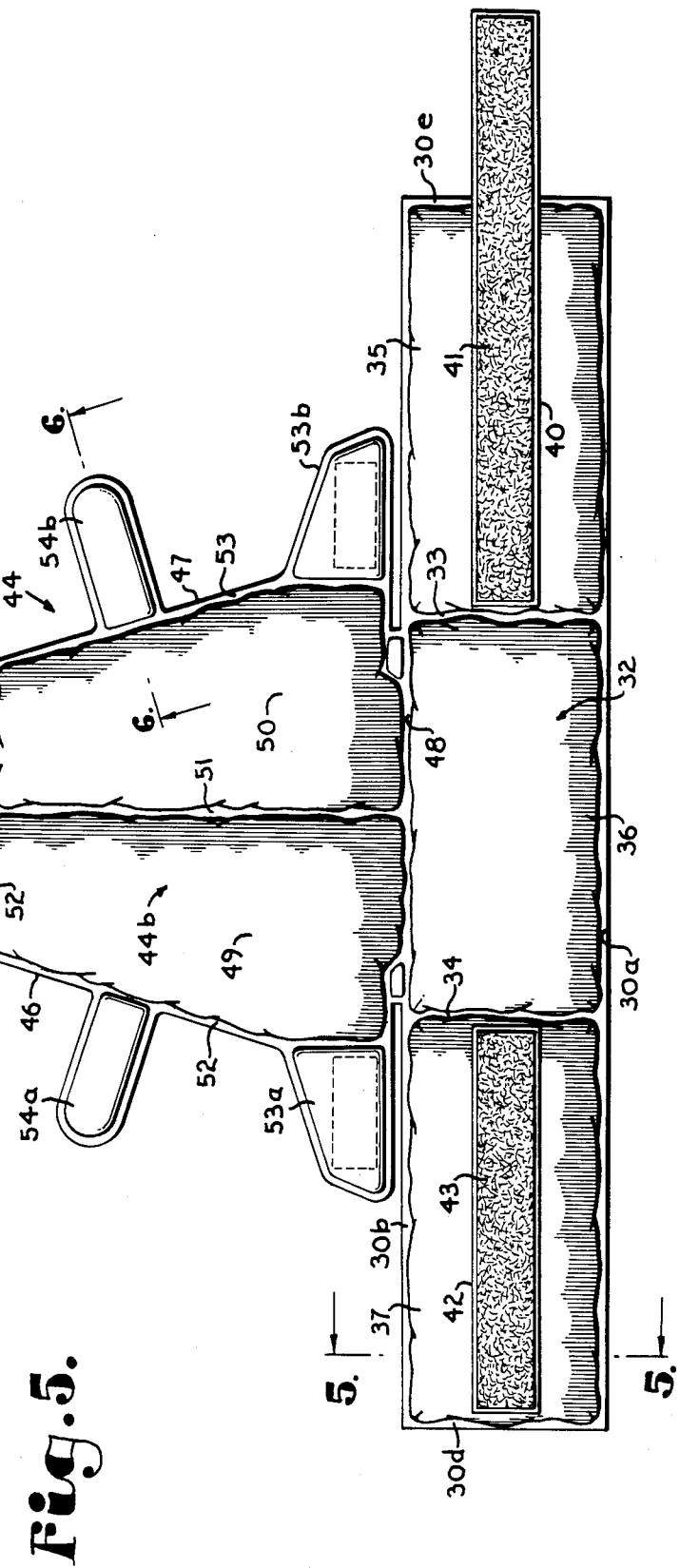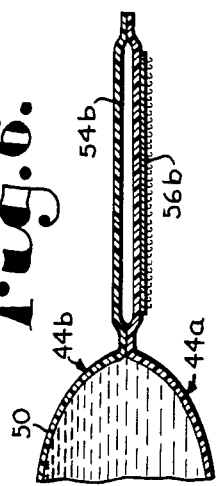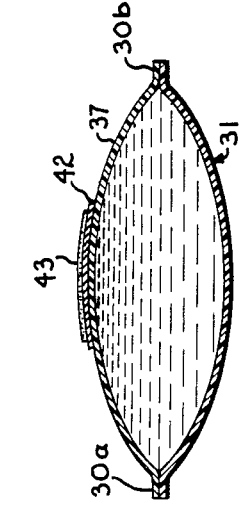

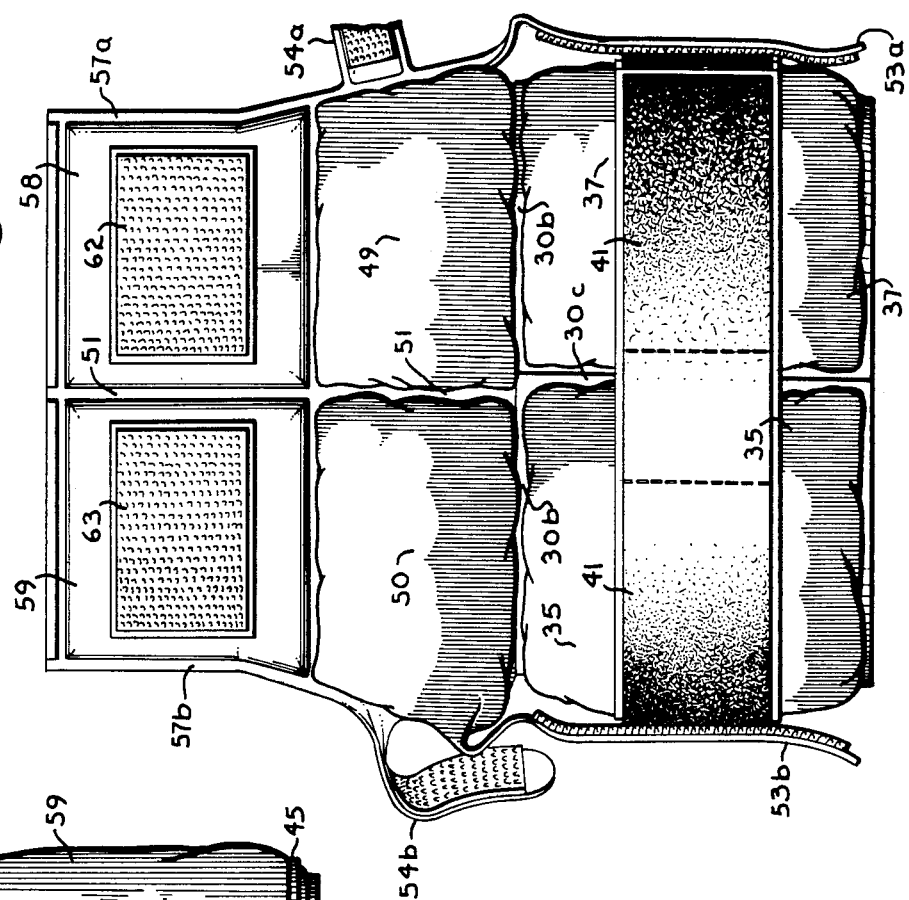
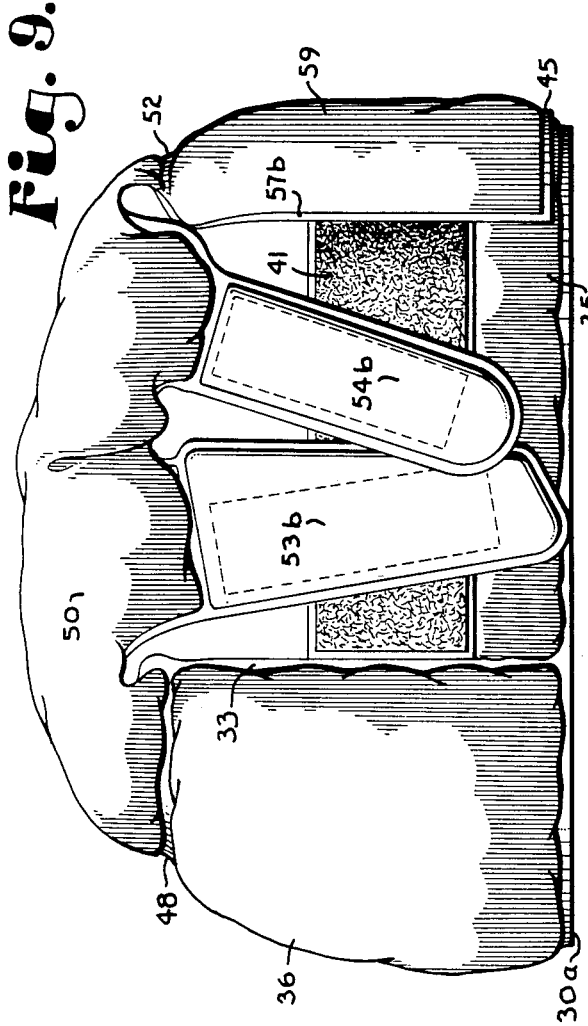
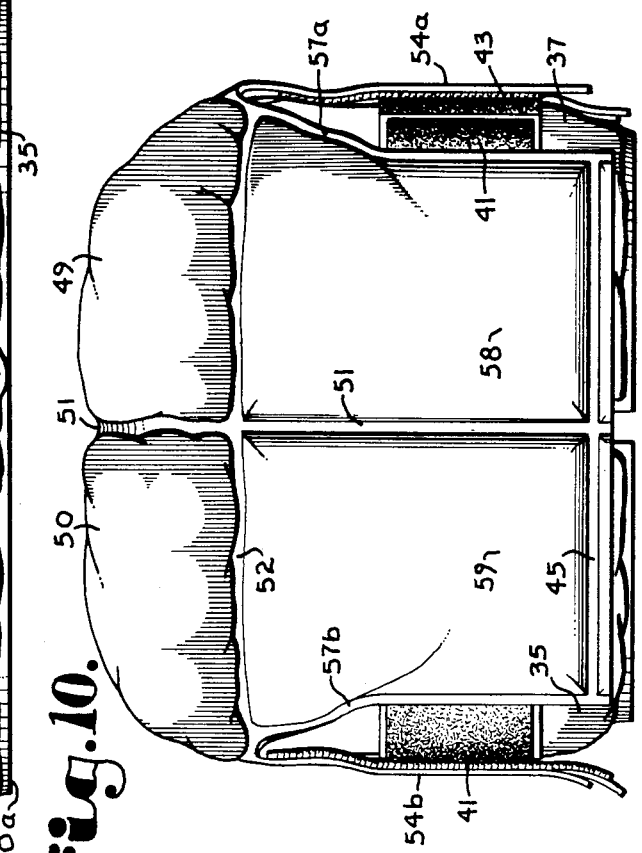

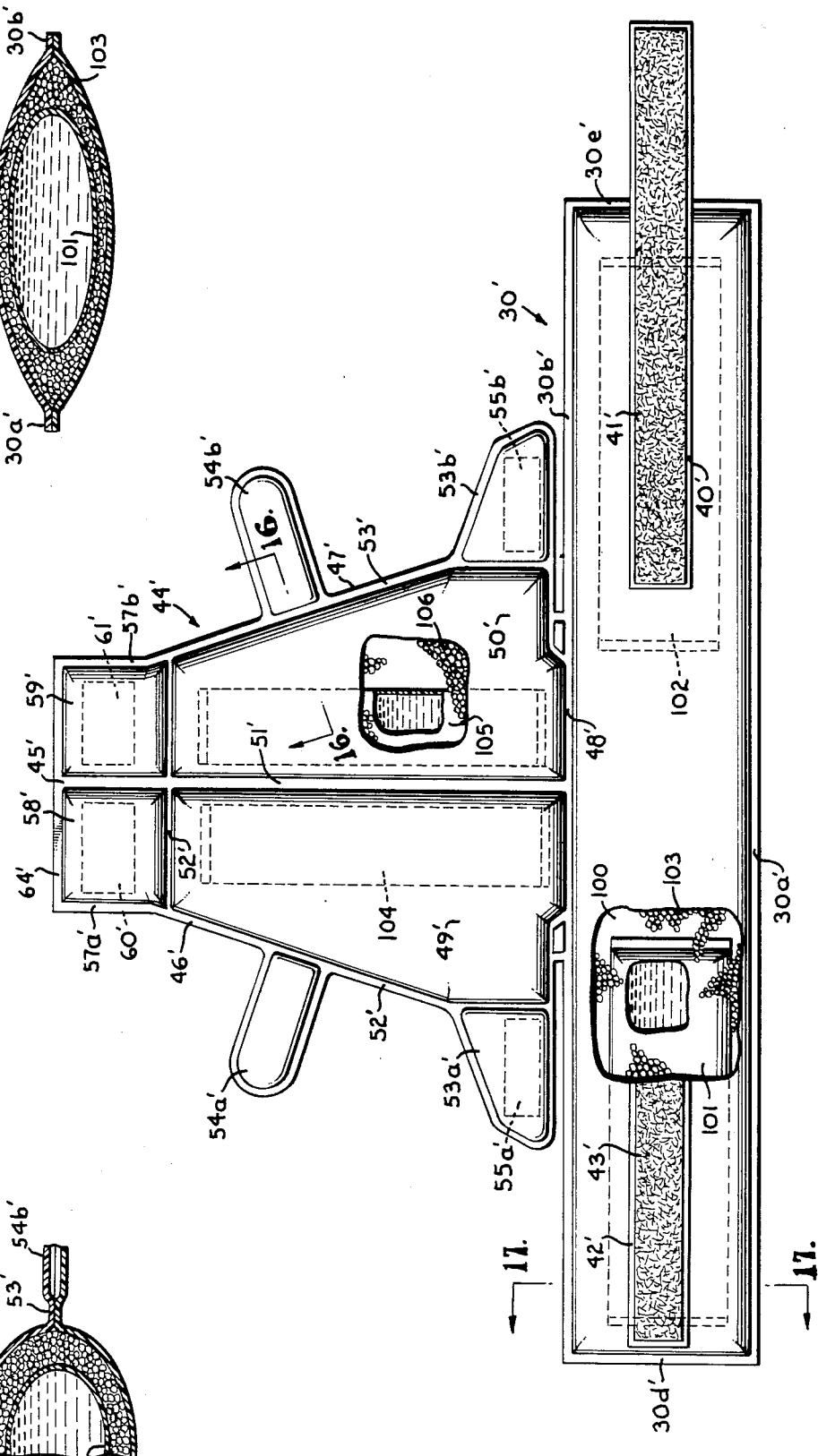

REUSEABLE HEAT TRANSFER DEVICES FOR THE SCALP

BRIEF DESCRIPTION OF THE INVENTION

One primary purpose of the subject device (in its primary application) is to chill substantially the entire hair bearing area of the scalp before, during and after a chemotherapy injection in order to minimize the quantity of such chemicals that reach (through the human blood stream) the hair roots or follicles. This is accomplished by three actions particularly enabled by the particular and unique construction of the subject reuseable device:

(1) Mild (adjustable for head size) constriction around the patient's head at the forehead-temple-rear skull base level by the headband portion of the device which action cuts down blood circulation into the scalp area;

(2) Chilling of all blood rising through the head circulatory system into the scalp area by cold transmitted through the headband portion, per se, circumferentially of the head; and (3) Essentially whole-scalp cold contact effected by a multiplicity of cells (three in the headband and two in the crown portion) containing heat exchanging material, such created by first fastening the headband in a constrictive relationship and then fastening the crown portion to the headband in a compressive relationship.

The subject device must not only provide mild constriction and compression with cooling heat exchange, but also must last for approximately an hour. First, in optimum procedure, the entire device is refrigeratively cooled before application of the device to the head of the chemotherapy subject some fifteen minutes before the chemotherapy injection. In such case, the entire scalp zone is precooled and blood circulation into the scalp zone, as well as therewithin, is impeded by blood vessel contraction through cooling (artery-vein-capillary) before treatment. The total course of a typical injection is 30 minutes. The subject device remains on the patient's head continuously during the injection, as well as the noted 15 minutes therebefore. Thereafter, following the chemotherapy injection, the subject device optimally remains on the patient's head for an additional 15 minutes. The chemotherapy chemical is presumably (typically) metabolized, deactivated or absorbed in the body by the end of this time.

It is well known in the prior art to employ the use of a constrictive band around a patient's head in chemotherapy to impede circulation to minimize hair loss. This serious impedance of circulation (which is required by the use of a constrictive band alone) is not only painful, comprising severe treatment, but potentially dangerous to the patient due to vessel compression and severe circulation restriction during treatment. The subject combination of cooling and mild constriction by the headband, such coupled with mild compression in the crown portion, is, at the very least, equally effective to the named drastic treatment and, in most cases, far superior in effect thereto, without the stress and noted problems of the constrictive band alone.

The concept of cooling the scalp of the chemotherapy patient to retain hair during actual chemotherapy is further not novel, per se. Ice pack applications have been known to prove effective. Applicants are also aware of the use of a multi-cellular, helmet-like cap having (typically) four segments useable for the same purposes of the subject device. The latter employs two side segments, one top segment and one rear segment, to applicant's knowledge. It is also known to employ refrigerable (nonfreezing, moldable) liquids (familiar to the art from long known prior art freezer cooled cold packs used for various purposes) in the place of endothermic reaction materials.

Deficiencies in the prior art devices which are cured by the subject invention include essential removal or prevention of "holidays" in the scalp heat exchanging device at any seams thereof. Yet further, new in a reuseable scalp heating exchanging device, there is mild constriction, totally independent of the crown heat exchange of the head, provided around the forehead-temple-skull base zone. Full cooling of not only the entire, noted headband constriction zone is provided, but, additionally, a continuous, compressive contact of heat exchanging cold over the entire upper head.

This device is an improvement and development of the device shown in U.S. patent application to Donald E. Truelock, et al, Ser. No. 199,738, filed Oct. 23, 1980 for "Heat Transfer Devices For The Scalp". This subject invention and improvement is a further development of that concept and invention, particularly in providing a reuseable device and function.

In the use of devices employing rerefrigerable substances, it is necessary to avoid, by careful control of freezer temperature, the chilling of the reuseable device to an excessively low temperature which will cause frostbite problems. Yet further, with a reuseable device, because of the highly personal nature of the subject described treatment, the possibility of cross infection between patients, the necessity of cleaning between uses, the requirement of storage between uses and, as well, the necessity of providing a suitable, controlled refrigeration source at or adjacent the chemotherapy area, numerous contingencies must be met and provided for.

The subject device essentially comprises the following elements (listed without limitation, including optional elements):

(1) A basic multicellular (preferably three cell) headband portion fabricated to be larger than a normal subject's head diameter, whereby to provide an overlapping wrap therearound;

(2) A crown portion or top section preferably comprising two skull top overlying cells running at right angles to the front one (or parts) of the headband portion cells, such preferably permanently connected to the headband at the top edge thereof and at the forehead overlying portion thereof;

(3) A rear headband attachment strap fixed at one end on one side of the basic headband portion, such adapted to overlie and removably stick to the other end of the headband portion in headband size controlling relation, as well as constriction controlling relationship; and (4) Attachment tabs on the crown portion (laterally positioned of the two overlying heat exchanging cells in the crown portion) for attachment of the sides of the crown portion to the sides of the headband overlying the subject's temples.

Hereinafter is disclosed and described a reuseable scalp heat exchanging device of great utility and efficiency which particularly involves and employs:

(1) A head encircling, size adjustable, constriction adjustable, multicell heat exchanging headband portion;

(2) A head top overlying, contacting and heat exchanging crown portion which is adjustably connectable (for head size, constriction and compression) between the front and rear portions of the headband in a fitting and fittable manner; and (3) Suitable connection and engaging means for intergrating, compacting and molding together the entire assembly, on a patient's or subject's head of (a) heat exchanging headband and (b) heat exchanging crown portion, so that the entire hair bearing scalp zone, or almost all thereof, is essentially under uniform heat exchanging contact, constriction and compression with greatest (adjustable and controllable) constriction in the headband zone and, effectively continuous, minimum holiday, heat exchanging contact over the patient's entire scalp.

Stated otherwise, absolute maximal, uniform, heat exchange is provided, with carefully controllable compression and constriction not only over the entire scalp zone but, most particularly, in the critical headband zone, where the basic blood circulation into the scalp area and head top area originates and exits. Thus, safety and comfort are maintained to the maximum degree, yet heat exchanging efficiency is not in any way sacrificed.

Other applications (without limitation) include the cooling of the head in case of certain types of trauma to inhibit bleeding after initial treatment of injury; cold and/or heat application to the entire upper head zone in the case of headache or migraine; use and preparation of the head and scalp zone for surgical penetration into the head in neurosurgery and the like. The pressure constriction option in the headband may be employed or not as required. With or without the latter, complete, uniform, upper entire head exchange may be obtained by use of the subject device.

Because the head piece construction of the subject primarily reuseable device is a significant improvement and development over the earlier invention to Truelock et al, Ser. No. 199,738, supra, the subject improved head piece construction is also available for use in a nonreuseable or one shot configuration. Truelock et al Ser. No. 199,738 shows one form (and a cheaper form) of a non-reuseable heat exchanging head piece. However, the instant device improves thereover in ease of applicability as well as fine adjustability of fit. Accordingly, as an option, applicants have additionally developed this device for a one shot, nonreuseable use. The only differences in the latter over the inventive reuseable structure shown in this case comprise:

(1) The substitution of actuatable, one-shot heat exchange means (such as granular ammonium nitrate and water bags in the cells for the cooling use); and (2) The provision of the head band portion preferably formed as a single cell, rather than a multiplicity of cells, so that the liquid portion of the heat exchanging mixture (such as water held in water bags prior to activation of the device) may fully mix with the heat exchanging chemical (such as ammonium nitrate in the cooling function). Thus, we have, in the subject invention, additionally provided improvements in nonreuseable or one shot applications of the heat exchanging head piece, as well as in the reuseable sort.

THE PRIOR ART

Applicants are aware of the following prior art references and patents which relate to (1) the use of cold (or scalp hypothermia) in cancer chemotherapy, (2) heat exchange of the body (parts thereof), (3) means therefor and (4) head (or parts thereof) heat exchange, particularly cooling.

With respect to loss of hair in cancer chemotherapy and the prevention thereof, particularly see "Prevention Of Adriamycin-Induced Alopecia With Scalp Hypothermia", authors Judith Beam, R.N., M.S., Sydney E. Salmon, M.D. and Katherine Griffith, R.N., New England Journal Of Medicine, December 1979. This article additionally cites 13 references with respect to chemotherapy, adriamycin, hair loss in cancer chemotherapy and prevention of hair loss by scalp cooling of patients receiving adriamycin (doxorubicin).

Applicants are aware of the following patents directed to heat exchanging caps for the scalp which include the concept of cooling:

Werrick, U.S. Pat. No. 770,031, issued Sept. 13, 1904 for "Hat Provided With Receptacle";

Morris, U.S. Pat. No. 1,627,523, issued May 3, 1927 for "Face Mask"; Zelony, U.S. Pat. No. 3,092,112 for "Therapeutic Compress" issued June 4, 1963;

Andrassy, U.S. Pat. No. 3,463,161 "Temperature Maintaining Device", issued Aug. 26, 1969;

U.S. Pat. No. 4,118,946 Tubin, "Personnel Cooler", issued Oct. 10, 1978;

Zebuhr "Slurry Cooling Of Helmets", U.S. Pat. No. 4,172,495, issued Oct. 30, 1979.

The following patents are directed to localized cooling of parts of the body, sometimes including parts of the head:

Meinecke, U.S. Pat. No. 919,614 "Hot Water Or Ice Bag", issued Apr. 27, 1909;

Baker, U.S. Pat. No. 3,491,761 "Adjustable Ice Bag Harness", issued Jan. 27, 1970;

Morse, U.S. Pat. No. 3,545,230 "Flexible Cooling Device And Use Thereof", issued Dec. 8, 1970;

Berndt, U.S. Pat. No. 3,717,145, issued Feb. 20, 1973 for "Cold Pressure Bandage";

Pilotte, U.S. Pat. No. 3,822,705 "Refrigerant Wrap For An Animal's Limb", issued July 9, 1974;

Lebold, U.S. Pat. No. 3,809,684 issued June 17, 1975 for "Hot and Cold Pack";

Pelton, U.S. Pat. No. 4,055,188 issued Oct. 25, 1977 for "Therapeutic Wrap".

The following patents are directed to heating devices for the scalp or head:

Larson, U.S. Pat. No. 1,710,882 "Scalp Treating Device", issued Apr. 30, 1929;

Hyer, U.S. Pat. No. 3,134,891 "Neck And Face Dry Heat Applicator", issued May 26, 1964;

Hariu, U.S. Pat. No. 3,839,621, issued Oct. 1, 1974 for "Body Heating Device";

Mantell, U.S. Pat. No. 3,908,569, issued Oct. 26, 1976 for "Heated Head Enclosure";

Murray, U.S. Pat. No. 4,061,898 issued Dec. 6, 1977 for "Heat Cap"; and

Walter et al, U.S. Pat. No. 4,147,921, issued Apr. 3, 1979 for "Heat Treating Articles".

A device for local cooling of extremities, including the head, by hypothermic spray of the area is seen in Smirnov, U.S. Pat. No. 3,587,577 "Device For . . . Hypothermy . . .", issued June 28, 1971.

As previously noted, this application is a particular improvement over the construction of Donald E. Truelock, et al seen in U.S. patent application Ser. No. 199,738, filed Oct. 23, 1980 for "Heat Transfer Devices For The Scalp."

OBJECTS OF THE INVENTION

The basic object of the invention is to provide greatly improved reuseable means, devices and processes for the effective application of cooling to substantially the entire hair bearing area of the human scalp to aid in prevention of hair loss during cancer chemotherapy.

Another object of the invention is to provide such reuseable means, devices and processes which supply and effect such cooling for a sufficient time, to the proper degree and without excess cooling or freezing (when refrigerated to the proper degree and temperature before use), in a most efficient and effective manner.

A further object of the invention is to provide such reuseable means, devices and processes wherein there additionally is provided some adjustable circulation limitation into and out of the scalp area by adjustable mild constriction of this zone, or the lower periphery thereof (including the forehead), the circulation limitation provided in the proper head position and area (approximate cap or hat headband area) and further cushioned for comfort to the subject, patient or user.

Another object of the invention is to provide substantial improvements in the construction, devices and processes of the U.S. patent application to Donald E. Truelock et al, Ser. No. 199,738, filed Oct. 23, 1980 for "Heat Transfer Devices For The Scalp", particularly in the realm of reuseable such devices.

Another object of the invention is to provide such reuseable means, devices and processes which may be applied to any individual's head within the normal range of sizes and shapes, regardless of head size and/or shape, with reasonable ease of application, the device requiring (for optimum application) but a single helper, the ultimately applied reuseable device being snug and comfortable on the subject's head after application, such easily and readily removable therefrom after performance of the chemotherapy injection for storage, cleaning, recooling and reuse as desired or required.

Another object of the invention is to provide such reuseable means, devices and processes which are rugged in construction, simple in structure for both application and removal, readily clean and stored, and having a long life under repeated and continuous usage.

Another object of the invention is to provide such reuseable scalp heat exchanging devices which provide, through proper application permitted by the structure thereof, substantial total area contact of the human scalp area for heat exchange, particularly for cooling in a chemotherapy application, when once applied. Such contact is without or with minimal "holidays" which might result in hair loss or possible hair loss (in the chemotherapy application) if such were present. With proper application, substantially full and continuous scalp application and heat exchange is provided, both in the headband zone and the crown zone of the device. Additionally, the cooling constriction provided in the headband minimizes the effect of the presence of any head contact holidays permitted by the presence of seams.

Another object of the invention is to provide such reuseable scalp heat exchanging means, devices and processes wherein several practical, convenient structural means of adjustment during application of the device are provided, both in the headband and crown zones, which means may be efficiently employed to effect snug, proper, continuous contact fit over substantially the entire human head scalp area. (The process of application first involves the headband application and fit which optionally may include adjustable constriction of the device to diminish blood circulation into the scalp zone. Thereafter, once that fit is properly effected, a crown zone application and fit is made. The latter completes assembly of the overall scalp contacting cap construction with a separate adjustment, such independent of, yet connected to the headband zone, in such manner that any user head size and shape (or combination thereof within the normal human range) may be readily adapted to and effectively and completely fitted and properly heat exchanged for whatever application is desired.

Still another object of the invention is to provide a reuseable, chemotherapy-associated, upper head portion cover which maximally protects the patient's head against hair loss by providing a combination of (1) around-the-head constriction and (2) continuous contact scalp heat exchange (cooling, for maximum effectiveness in minimizing and preventing hair loss due to the physiological action of drugs used in cancer chemotherapy).

Another object of the invention is to provide such reuseable structures, devices and processes which are (1) mass produceable, (2) uniform in structure and operation, (3) long term storeable without deterioration under proper conditions, (4) sanitary in use if initially clean and (5) readily cleanable, storeable and rechillable after a given use and application.

Yet another object of this invention is to provide a reuseable segmented or multi-cellular heat exchanging device for the entire human hair-bearing scalp area wherein the safety, convenience and utility of a multicellular device is present, yet wherein the device is readily, easily and conveniently applied to the patient's head and scalp in such manner that the necessary seams between the cells minimally act (in the headband and crown areas as nonheat exchange or "holiday" zones, there being provided essentially continuous, pressurized contact against the subject's head of the cellular, heat exchanging material carrying parts of the device when applied.

Another object of the invention is to provide reuseable devices, constructions and processes of the character described, wherein there are provided separate, multi-cellular headband and crown heat exchanging areas or zones, yet wherein, when the device is assembled and applied to the head of the chemotherapy patient or user for any application, in proper manner as an assembled cap, there is a substantially unitary, substantially continuous body of cooling of heat exchanging surface applied to the subject's or user's head.

Yet another object of the invention is to provide new, reuseable means and methods of the character described for heating or cooling (depending on the heat exchange applied to the device before use) of substantially the entire upper head zone of a patient or person in new, effective and efficient ways, without discomfort to the patient or threat of injury or damage to the anatomy or physiology of the patient's head.

Yet another object of the invention is to provide a nonreuseable, one shot, heat exchanging head piece which incorporates, to a large extent, the improvements of the subject reuseable head piece and thus further improves over Truelock et al U.S. Ser. No. 199,738, supra, particularly with respect to ease of applicability and ability to well and precisely fit the head of the user.

Another object of the invention is to provide an improved heat exchanging head piece involving a single cell head band and a multicell crown portion, the cells in the crown and head band portion having heat exchanging materials therein of the type wherein mixing of a liquid portion thereof with a dry portion thereof creates endothermic or exothermic effects.

Still another object of the invention is to provide a new heat exchanging head piece construction which is readily applied and removed, the construction being provided, alternatively, as a reuseable construction or a nonreuseable, one shot construction, each configuration having an optimum structure for application, use and removal wherein the maximum heat exchanging effect most advantageous to the patient is achieved with minimum or no detrimental effects.

Other and further objects of the invention will appear in the course of the following description thereof.

THE DRAWINGS

In the drawings, which form a part of the instant specification and are to be read in conjunction therewith, an embodiment of the invention is shown and, in the various views, like numerals are employed to indicate like parts.

FIG. 1 is a bottom, inside view of the empty blank for the subject scalp heat exchanger before the cells of the blank are filled with chemical material for repeated refrigeration and/or heating and thereafter sealed. A part of the figure is cut away in one portion to better illustrate the construction of one filler opening for one headband cell. This figure shows the lower, inside surface of the device (when assembled and in use on a patient) which lies against the scalp of the patient.

FIG. 2 is a view taken along the line 2—2 of FIG. 1 in the direction of the arrows (with the walls of the blank expanded apart from one another for clarity in visualizing the separate layer constructions thereof).

FIG. 3 is a view taken along the line 3—3 of FIG. 1 in the direction of the arrows (with, again, the walls of the blank expanded away from one another to better illustrate the separate constructions thereof).

FIG. 4 is a vertical plan view of the laid out device of FIG. 1 taken from the opposite side thereof (comprising the outside with respect to application to a patient), with the cells of the blank filled with heat exchanging or temperature effective material and sealed to contain such.

FIG. 5 is a view taken along the line 5—5 of FIG. 4 in the direction of the arrows.

FIG. 6 is a view taken along the line 6—6 of FIG. 4 in the direction of the arrows.

Figure 7:
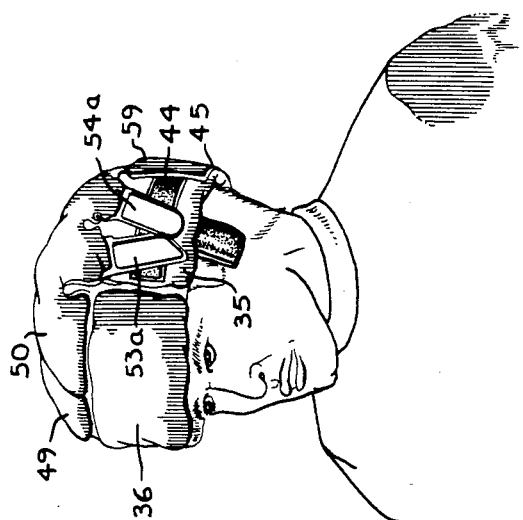

FIGS. 7-12, inclusive comprise various views from various vantage points of the device assembled together in the manner of application to a user's, subject's or patient's head. However, FIG. 7 is the only view which shows the patient's head.

FIG. 7 is a three-quarter perspective view from the front and slightly to one side of the head of a subject with the instant device finally assembled and engaged in use arrangement on the subject's head, such essentially adjusted for substantially full scalp heat exchange.

Figure 8:
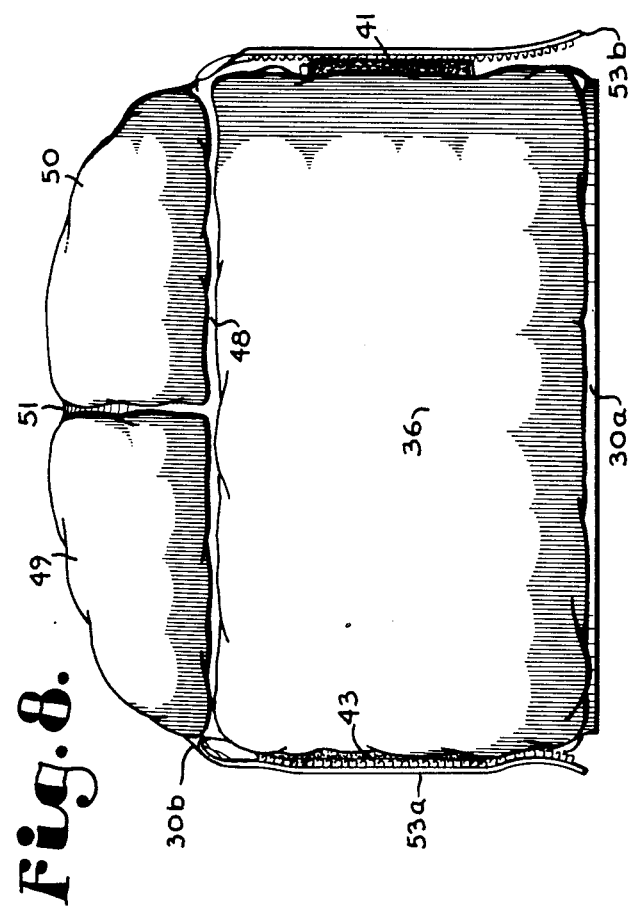

FIGS. 8-10, inclusive show the assembled device of FIG. 7 (without the subject's head therein) in three views, sequentially, in order: front, side and rear views.

FIG. 8 is a front view of the device of the subject invention in assembled form.

FIG. 9 is a side view, taken from the right hand side of FIG. 8 looking to the left in the view (or from the right hand side of FIG. 7 looking to the left in the view).

FIG. 10 is a rear view of the assembled device of FIGS. 7-9, inclusive.

Figure 11:
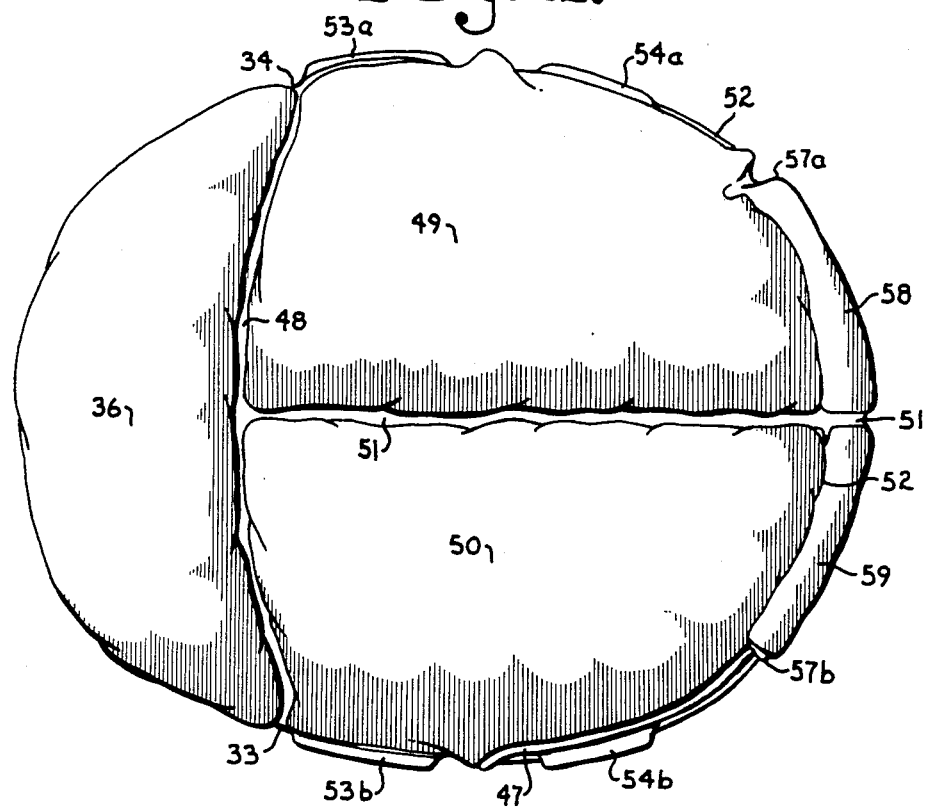

FIG. 11 is a top plan view of the assembled device of FIGS. 7-10, inclusive with the front of the device to the left in the view of FIG. 11.

Figure 12:
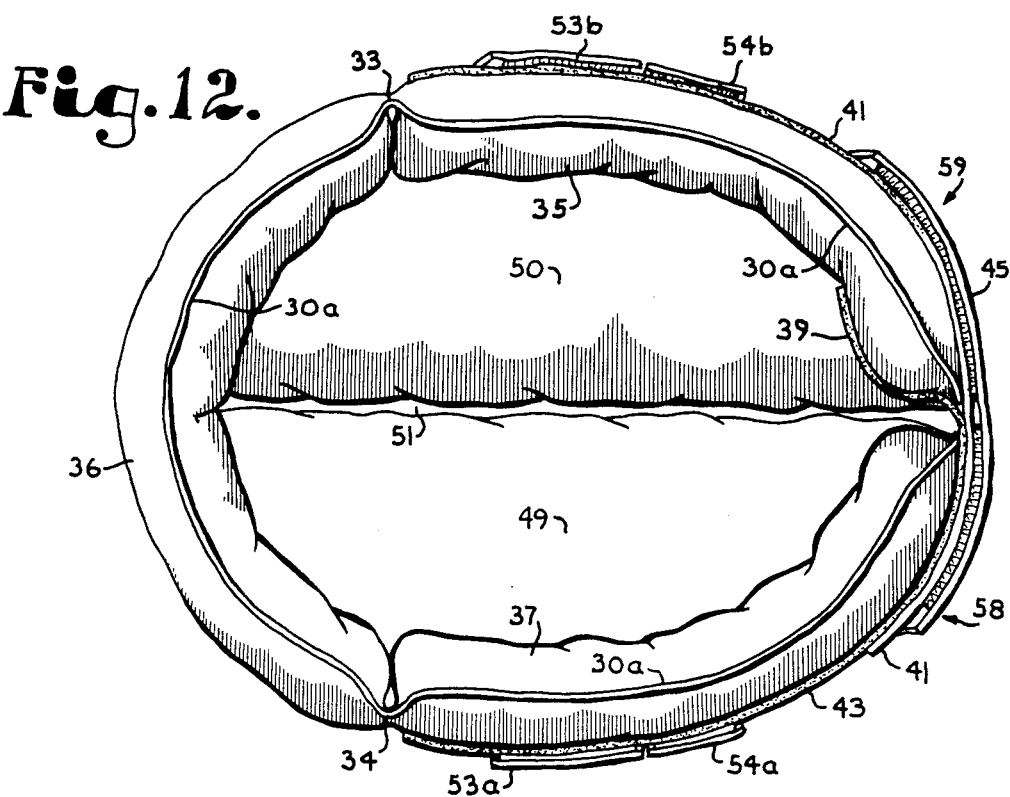

FIG. 12 is a bottom view of the assembled device of FIGS. 7-11, inclusive with the front of the device to the left in the view of FIG. 12.

Figure 13:
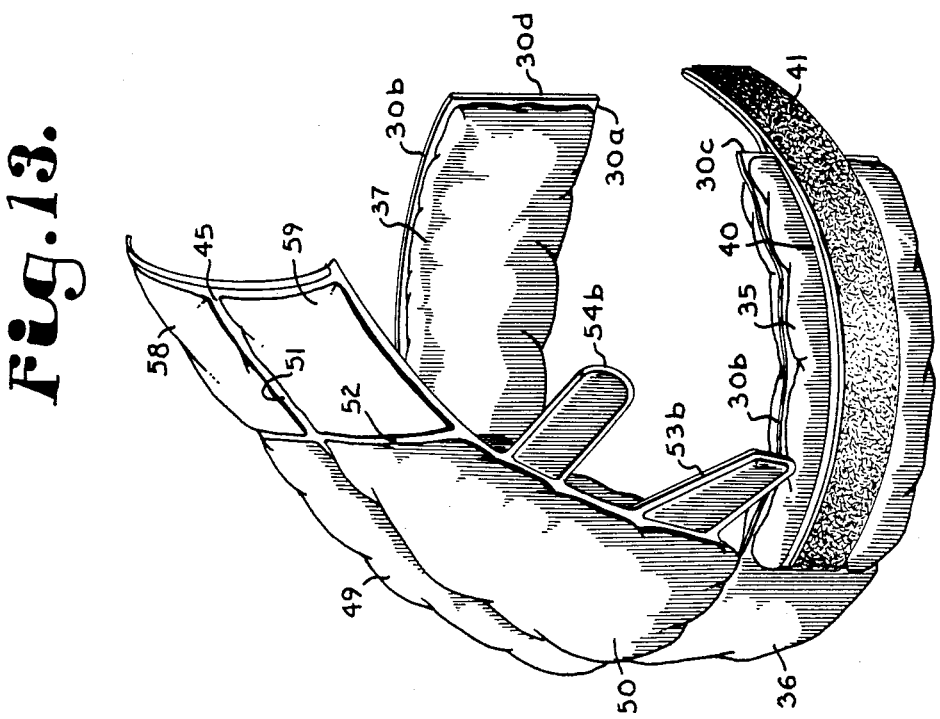

FIG. 13 is a three-quarter perspective view of the device of FIGS. 4-12, inclusive taken from above and slightly to the rear in a first stage of application to the head of a patient or subject (absent that head) as the headband is first being wrapped about the subject's head.

FIG. 14 is a rear view of the device of FIGS. 4-13, inclusive, showing a later stage of assembly than that of FIG. 13 (after the headband portion has been secured in desired constrictive relationship and the forward engagement tabs of the crown portion have been secured to the headband sides), but prior to securement of the back end of the crown portion on the rear portion of the headband and also prior to the engagement and securement of all the rear lateral crown portion tabs on the rear headband side portions).

FIGS. 15-17, inclusive are directed to a showing of the subject improved device adapted to a nonreuseable or one shot use. Specifically, the differences in this construction over the construction seen in the previous figures lie in:

(1) The head band being a single continuous cell, rather than three separate cells; and (2) The cells of the headband and crown portions receiving nonreuseable heat exchange materials (such as rupturable water bags and quantities of granular ammonium nitrate for the cooling function).

FIG. 15 is a vertical plan view of the laid out device (or filled blank form) taken from the outside with respect to application to a patient, portions of the headband and one of the crown portion cells, as well as one of the water bags in the latter, cut away to better illustrate the subject construction.

FIG. 16 is a view taken along the line 16—16 in the direction of the arrows.

FIG. 17 is a view taken along the line 17—17 of FIG. 15 in the direction of the arrows.

FIGS. 18-21, inclusive show additional details of the application and use of the reuseable device of FIGS. 1-14, inclusive in stages of application thereof to the head of a patient.

Figure 18:
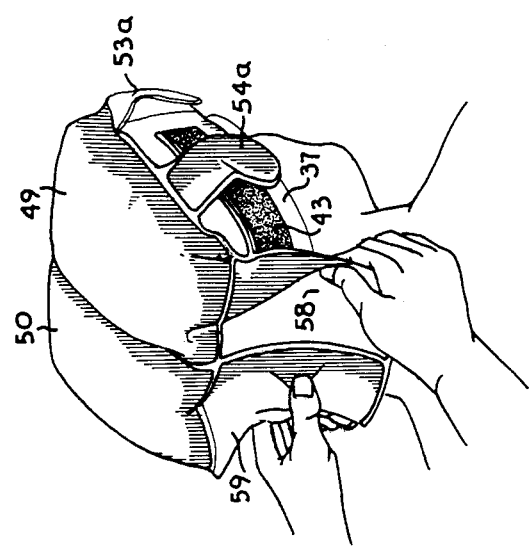

FIG. 18 is a rear perspective taken from above of the device of FIGS. 1-14, inclusive applied to the head of the patient with the view taken in sequence between the assembly stage of FIG. 14 (before the rear flap of the crown portion is secured) and the fully assembled structures of FIGS. 7-12, inclusive.

Figure 19:
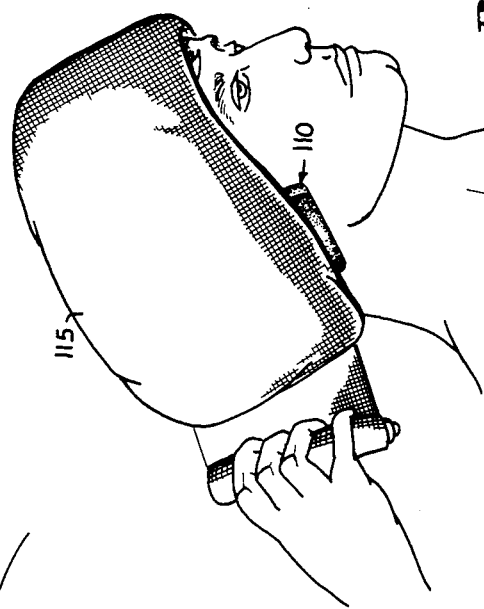

FIG. 19 is a view taken subsequent to the view of FIG. 7 (full assembly) and shows the wrap of an elastic bandage over the device for purposes of uniform contact and compaction of the heat exchanging cells of the head band portion with respect to the head of the user and one another.

Figure 20:
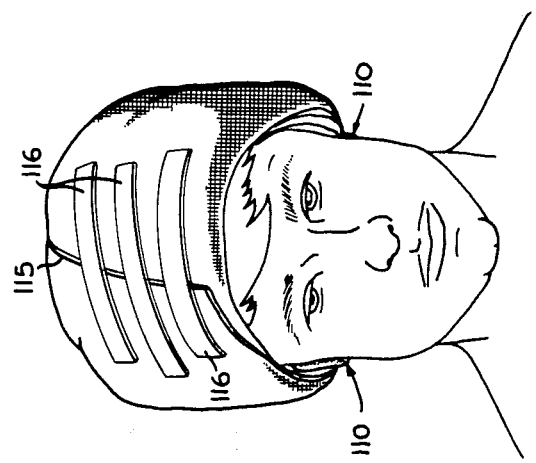

FIG. 20 is a frontal view of a patient after the application of the elastic bandage of FIG. 19.

Figure 21:
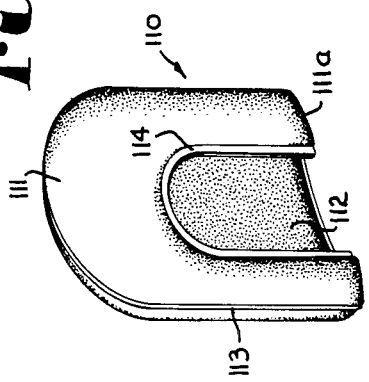

FIG. 21 is an enlarged detail of an ear protector construction which may be seen applied to the ears of the users of the device in FIGS. 7 and 19.

RATIONALE OF THE INVENTION

In order to clearly and unquestionably understand the significance of the described and illustrated scalp heat exchanger, the following information is extracted and paraphrased from the Beam, Salmon and Griffith article mentioned in the above entitled section "The Prior Art".

The psychological impact of chemotherapy-induced alopecia (hair loss) represents one of the more devastating side effects of cancer chemotherapy. In some instances, the psychological consequences of this lead patients to refuse potentially curative chemotherapy. The hair loss problem is severe with the anthracycline antibiotic Adriamycin (Doxorubicin), a chemotherapy compound which has a spectrum of efficacy incompassing many types of cancer (e.g., breast, lung and ovary sarcomas, lymphomas and leukemias).

As early as 1973, an Abstract was published reporting good protection against Adriamycin - induced hair loss in 12 or 15 patients by regional application of chilled air to the scalp. More recently, the use of cryogel packs held on the scalp with stockingette produced good protection against hair loss over a short time in 20 to 40 patients on the same therapy.

It would appear that two advantages could accrue from cooling the scalp (scalp hypothermia). The first of these is vasoconstriction resulting from such, which decreases the amount of drug reaching the hair follicles. Secondly, Adriamycin (as numerous other drugs) requires temperature-dependent metabolic processes for cellular uptake and thus would have decreased action at reduced temperature.

In Beam et al the study involved the prophylactic treatment of cancer patients receiving adriamycin-cyclophosphamide combination chemotherapy with a brief scalp hypothermia procedure at the time of each injection. The particular procedure described used crushed ice and disposable plastic bags. This treatment proved to be simple, inexpensive, well tolerated and universally available. It further proved to be quite effective in preventing hair loss and the patients studied had good or excellent preservation of scalp hair, usually obviating the need of wigs for cosmetic purposes. An even higher portion of patients receiving chemotherapy doses of lesser strength had good protection. Thus, it would seem that the protective scalp cooling was, to a certain extent, inversely related to dosage, so that a longer duration or more profound cooling might prove useful to consistently prevent hair loss at greater dosages.

In the actual Beam et al procedure, foam pads cut from the heels of disposable hospital slippers were placed over the patient's ears to insulate them against excessive cold exposure. Ice packs consisting of crushed ice in 60 by 60 centimeter plastic bags were applied (one in front, one in back) to cover the entire scalp. The ice packs were secured with 15 centimeter size Ace bandages wrapped in turban style. Such a turban was applied 5 minutes prior to each injection and left in place 30 minutes following the injection for a total of 35 to 40 minutes of scalp cooling.

The noted scalp iceing procedure reduced Adriamycin-induced hair loss substantially in relation to extensive prior historical experience with that drug combination. Good protection against hair loss was frequently maintained for the full 6 to 8 months period of drug administration. In the article, it should be noted, it was also hypothesized that a longer initial cooling interval perhaps should be employed.

STRUCTURAL AND HEAT EXCHANGE MATERIALS

The basic purpose of the subject invention is to cool the scalp areas of chemotherapy patients (together with limited scalp zone constriction) in order to prevent hair loss in cancer chemotherapy. However, the subject construction and development is not limited to such use or mere cooling. Specifically, that is, the entire construction may alternatively be used as a scalp heating cap, device or cover merely by heating the device before application rather than cooling in a freezer. In such use, the construction of the device would be the same, however with heating produced rather than cooling upon application to a patient's head. A proper filler able to withstand either or both repeated heating and cooling must be employed in the cells of the device, depending on its purpose.

Typical, but not limiting, gel or reuseable fluid materials employable in the cells of the subject device in body heat exchange are seen in some of the patents above listed, including Zelong 112, Andrassy 161, Morse 230 and Pelton 188. Also note Brennan, U.S. Pat. No. 4,190,054, issued Feb. 26, 1980 for "Therapeutic Bandage". One reuseable, typical heatable/chillable gel employable in this application in the cells of the subject structure could be composed of 40% glycerine, 52% distilled water and 8% starch. Suitable colored dyes and disinfectant substances (for example, formaldehyde) may be added to this formulation to enhance appearance and prolong life.

It is further well known in the art to provide (1) plastic films and laminate films (2) plastic film pouches, packages and containers and (3) heating or refrigerating package constructions of plastic film material. Typical materials making up such films include polyethylene, cellophane, polypropylene, polyester, etc. It is also known in the art to provide certain types of rupturable film packages and refrigerating packages, the latter seen in the Robbins et al patent, infra. Since polyethylene and polypropylene are heat sealable, they are also commonly used as the internal member of a film laminate in a package construction, with a polyester or cellophane layer comprising the external laminate layer. Laminate films seemingly seal better, and the seals last longer, than simple, non-laminate films.

The patent to Perino, U.S. Pat. No. 3,250,384, issued May 1, 1966, discloses (FIGS. 7-9, inclusive) cooling packages of the type described and, as well, various materials useful in the films for the respective containers thereof. It should also be understood that double wall polyethylene films or multiple layer polyethylene films may be used, as seen in the patents to Scholle, U.S. Pat. Nos. 2,898,027, Sachs 3,122,197, and, as well, the method patents to Anderson et al 3,130,647 and Makraur 2,721,691.

Polyethylene, polyvinyl and polymylar films of one or more layers or laminates may further conveniently be employed in this invention. A layer of non-allergenic paper may conveniently be laminated thereto for comfort, better skin sensation and condensation absorption (as an outside layer).

REUSEABLE AND SINGLE USE DEVICES

The construction of the particular instant disclosure and specification is one particularly adapted for and designed to be employed in reuseable or reuse situations. That is, the device is preferably to be used repeatedly in heat exchange of the scalp, without throw-away or destruction, until excessive wear occurs. Depending upon the cell filler materials, the heat exchange devices may be stored at room temperature or under refrigerating conditions.

The construction in the U.S. patent application Truelock et al Ser. No. 199,738, filed Oct. 23, 1980 for "Heat Transfer Devices For The Scalp" is one particularly adapted to single use or "one-shot" application where, within the cells of the device, a dry chemical and a bag of water mixable therewith are employed to produce an endothermic or exothermic reaction. However, alternatively, that construction, as spelled out in the noted application therefor, could be used employing a refrigerable (rerefrigerable) or heatable (reheatable) compound in the headband and crown section cells. In the instant case, the construction is optimally adapted to the reuse option (rechilling or reheating), but alternatively may be single use or one-shot.

In such latter case, known prior art systems and compounds may advantageously be employed. Refrigerating and heating packages (cold packs and hot packs) of a type containing, within the outer pack, a dry chemical and a bag of water mixable therewith (on bursting of the water bag) to produce an endothermic or exothermic reaction, respectively, are well known to the art. The patent to Robbins, et al U.S. Pat. Nos. 2,925,719, issued Feb. 23, 1950 for "Refrigerating Package" and the patent to Callouette, 3,643,665, issued Feb. 22, 1972, for "Therapeutic Pack For Thermal Applications" typically show the state of the art with respect to such. The water may be isolated from the particular dry chemical before activation by means other than bagging.

The Robbins et al patent, supra, discloses a refrigerating package including an outer envelope formed of a suitable, flexible, fluid-tight sheet plastic material (for example polyethylene, vinyl or acetate), an inner envelope formed of the same material, a quantity of dry refrigerating chemical such as ammonium nitrate within the outer envelope and a quantity of water or other hydrous chemical disposed within the inner envelope. When the package is to be activated, an inward squeezing force is manually applied thereto so as to effect the rupture of the inner bag. Upon such rupturing of the inner bag, the water originally contained therein mixes with the dry chemical so as to result in a solution having either a much lower or much higher temperature than the original temperature of the package.

The point to be made here is that the subject improved device may, in addition to employing chemical compounds, fluids or gels of the reuseable (rechillable and/or reheatable) type, may employ, alternatively, conventional single use or one-shot heating and/or cooling systems of the type just described. The outer container, in any case, may be single ply, multiple ply, a laminate of different materials or a plurality of plies of the same material or the like. The inner container or bag (if there is one) may be single layered, multiple layered, multi-ply, laminate, weakened for easy breakage or the like.

DESCRIPTION OF THE BLANK

Referring first to FIGS. 1-3, inclusive, therein is shown a blank for the subject human scalp heat exchanger before the cells of the blank are filled with heat exchange materials (or temperature effectable materials) for heat exchange. In further discussion, the terms "heat exchange materials" and/or "temperature effectable materials" will be taken to include either or both: (1) reuseable fluids, gels or substances which may be rechilled, reheated, or both, for multiple use of the device and (2) single use or single shot materials such as, for example, water bags and ammonium nitrate, in the case of a cooling or chilling combination. That the subject device is particularly employable for the reuseable function is shown by the filler openings shown and to be described for the headband portion cells. In the event that single use materials were to be employed therewith, these openings would be generally considerably larger for insertion of water bags, as well as granular endothermic material or exothermic material (upon mixing of water therewith).

As above described, FIG. 1 is a bottom or inside plan view of this empty blank (the side which is to be next to the scalp zone of the user), while FIGS. 2 and 3 are views taken along designated lines of the blank with the walls of the blank expanded apart from one another for clarity in illustrating separate cells thereof. In the views of FIGS. 2 and 3 and, as well, those of FIGS. 5 and 6, it can be seen that the walls of the blank and heat exchanger are shown as single ply. However, laminates, such as, typically, polyethylene or polypropylene on the inside with polyester or cellophane comprising the outer laminate layer, may be employed. For convenience in description, it will be assumed that each side wall of the portions of the blank or heat exchanger is monolithic in construction.

Also as previously described, it should be understood that the views of FIGS. 1 and 4 are inverted from one another with FIG. 1, the empty blank, showing the inner surface of the blank before filling. This is the surface next to the patient's head which is to be heat exchanged. On the other hand, FIG. 4 shows the outside surface of the filled heat exchanger with the heat exchanging materials sealed into the cells thereof. This is the surface of the device which is away from the patient's scalp or head in use.

Referring, then, first to FIG. 1, at the bottom of this view is seen an elongate rectangular headband portion generally designated 30. Headband portion 30 has lower edge 30a, upper edge 30b and free end edges 30c and 30d. Except for filler openings 30e, 30f and 30g in the lower edge 30a of headband portion 30, the entire headband portion 30 is peripherally sealed in conventional manner by a heat seal or ultra sonic weld, etc. Since the headband portion 30 has an inside wall generally designated 31 and an outside wall generally designated 32, such peripheral seal would provide a single, elongate cell or bag save for the filler openings noted. Optionally, such elongate single bag could be filled with granular ammonium nitrate (or other chemical) and one or more water bags in the manner disclosed in Truelock et al 199,738, supra. In such case, but a single large filler opening may be provided in the headband portion 30 or two larger such.

Preferably, however, additional heat seals or ultra sonic welds are provided at 33 and 34 thus to provide three cells or bags 35, 36 and 37 in the headband portion 30, each served by a filler opening. Each of these cells is to be filled with reuseable heat exchanging or temperature effectable material, chemical or substance or, alternatively, single use heat exchanging materials of the character previously described. In the latter case, again, where, typically, a water bag and a chemical such as ammonium nitrate would be typically employed, the filler openings would be of larger size. The cells 35-37, inclusive may be, and preferably are, of substantially equal size. Alternatively, they may be of different size with the center cell 36 either larger or smaller than the end cells 35 and 37. In the event cell 36 is of larger size than the end cells 35 and 37, it may hold a typical quantity of 550 grams with the outer cells holding 410 grams of heat exchange or temperature effectable material. In the reverse case, the center cell, as an example, may hold 410 grams, with the outer cells holding 550 grams. These are examples and not to be limiting. A tab 38 having removably engageable means or material 39 thereon is fixedly attached in a lesser portion of the length thereof to the inner face of cell 35 with a preferably greater length portion thereof extending past free end 30c for a purpose to be described.

Reference at this time is made to the lower portion of FIG. 4 which shows the headband portion of the blank in filled configuration from the opposite side. On cell 35, the outside face thereof (side 32 of the headband portion 30, per se), there is provided an elongate tab or strip 40 which, in the greater portion of the length thereof, overlies and adheres to the outer surface of cell 35. In a lesser length portion thereof, strip 40 extends past end 30c in a length equal to the free length of tab 39 on the other side thereof. These two free portions are fused or fixed together, one with the other. Removably securable or engaging material is provided on the external surface of tab 40 along substantially the entire length and width thereof as at 41. In FIG. 4, with respect to cell 37, on the outer face thereof, there is provided an elongate strip or length 42 which is secured fixedly to the said outer face of cell 37 in the position shown. Strip or length 42 has removably securable or engageable material 43 thereon in substantially the entire length and width thereof.

A crown portion generally designated 44 has a rear or rearward end and edge 45, side edges 46 and 47 and a forward or front end and edge 48 which is integral with or secured to the center of the upper edge of headband portion 30. In fabrication of the blank being described, two single ply or laminated sheets configured precisely to the configuration of the overall sheet of FIG. 1 may be laid, one on the other, in alignment with one another and heat or otherwise sealed to one another at the side, ends and edges, as well as interiorly thereof, in order to give the blank configuration being described (before filling). This is the preferred and optimum method of fabrication. The seals may be heat seals, ultrasonic welds or other connections optimum to the plastic single ply, multiple ply or laminate sheets employed.

Crown portion 44 has several parts. The first of these comprises two center, forward cells 49 and 50 which are separated from one another and interiorly defined by seal 51. They are exteriorly defined by edge seals 52 and 53 which run along the side edges 46 and 47, define the interior boundaries of tabs to be described and then move centrally at the forward portion of crown portion 44 to join, with and at top seal and connection 48, with head portion 30. Thus, edge seals 52 and 53 run into and are continuous with the upper edge seal 30b of headband portion 30 so there is a complete front end seal of compartments or cells 49 and 50, as well as a top seal to cell 36 of the headband portion, at 48. The rearward boundaries of cells 49 and 50 are provided, in filled condition (see FIG. 5), by transverse heat seal or ultrasonic weld (or the like) 52.

The second part (or parts) of the crown portion comprise paired sets of tabs 53a and 53b (forward on the crown portion) and 54a and 54b (rearward or intermediate on the crown portion). These tabs are unfilled (but substantially air exhausted) pockets defined by circumferential heat seals or ultrasonic welds, etc. Elongate strips, panels or lengths are fixed thereto on the inside surfaces thereof as at 55a and 55b on tabs 53a and 53b and 56a and 56b on tabs 54a and 54b. Removably engageable and securable material are fixed to the faces of these panels, strips securable material are fixed to the faces of these panels, strips a well known, commercial hook/loop plastic construction giving strong but removable and repeatable securement when pressed against like panels or strips of material.

The third part of crown portion 44 involves the rearward attachment flap generally designated 57 having parallel side edges 57a and 57b which are continuations of the edge seals 52 and 53, respectively. These comprise, in the unfilled blank, feed or loading channels 58 and 59 defined between the side edge seals and the center seal 51 extending into flap 57. On the inside surface of crown portion 44, which is generally designated 44a as opposed to the outer surface 44b, there are provided a pair of preferably rectangular panels 60 and 61 firmly attached to the inner wall of flap portion 57. These panels have removably securable or engageable material of the character previously described at 62 and 63 thereon. Referring to FIG. 4, at the top thereof, there is seen the end seal 64 which serves to seal off the feed channels 58 and 59 after the cells 49 and 50 have been filled with reuseable temperature effectable material or single use heat exchanging materials, etc. The end tabs, then, are unfilled cells circumferentially sealed upon themselves, but preferably substantially air exhausted.

Thus it may be seen that what has been provided in the blank of FIGS. 1–3, inclusive comprises a multicelled, sealable blank optimally defined by sealing together identical sheets of laminated, single ply multi ply plastic, such configured in a certain manner. Each of the cells or compartments has an open end or filler opening for filling.

THE FILLED BLANK

In order to more adequately describe the blank structure and sealing thereof, some discussion of the construction of FIG. 4 has already taken place. However, the filling of the blank, its completion and the filled blank, per se, will now be discussed.

With the construction provided and shown as described in FIGS. 1–3, comprising the assembled, heat (or otherwise) sealed blank with, however, access openings into each of the cells, compartments or bags 35–37, inclusive in the headband and 49 and 50 in the crown portion, filling may be undertaken. With respect to the headband portion 30, this typically involves, in the case of reuseable material, the insertion of the desired quantity of material or chemicals through the filler openings. This could take place in a following typical, but not limiting, manner.

Assuming a formula (somewhat different from that previously given) for a reuseable filler material in the reuseable device comprising distilled water 58.3%, medical grade glycerine (U.P.S 96) 39%, a standard gelling agent such as Carbopol 940 0.5% and liquid formaldehyde 0.2%, as well as sodium hydroxide of a 10% solution in water, filling and seal could be accomplished as follows. (It might be noted that the purpose of the glycerine is to prevent solid freezing, the gelling agent is to produce the desired gel, the formaldehyde is to prevent bacterial growth and the sodium hydroxide is to set the gel. The latter being the case, the water, glycerine, gelling agent and formaldehyde are first all mixed and comprise a liquid.)

With the materials prepared, the formed blank of FIG. 1 is then positioned, if it is desired to fill the headband cells first, with the lower edge 30a of the headband portion at the top of a vertical suspension of the blank with the rearward edge 45 of the crown portion hanging vertically downwardly therefrom. The mixture noted is then poured into filler openings 30e–30g, inclusive and the gel setter (NaOH) then added. When the gel is set, air is removed from the remainder of the cells 35–37, in question and the heat seals at 30a completed across openings 30e–30g, inclusive. The inlet spouts then may be trimmed off for uniformity. In the construction shown, the fill quantities could be as given elsewhere, typically, equal quantities of 410 grams, equal quantities of 550 grams or unequal quantities of 410 and 550 grams, as specific examples.

In filling of the cells 49 and 50, whether they are filled before or after the headband 30 cells 35–37, inclusive, the device may be suspended by suitable holders with the passageways 58 and 59 openable or open upwardly and the balance of the device extending substantially vertically downwardly therefrom. At this time, the mixture of water, glycerine, gelling agent and disinfectant or antibacterial agent, in the mix form, are poured into cells 49 and 50 in the quantity desired. As soon as they are filled, the gel setting agent, sodium hydroxide, may be added and the gel set. Once this is accomplished, the seal 52 is effected across the top of the cell portions, but below wall portions 57a and 57b and then the end heat seal 45 made. Air is preferably removed from cells 49 and 50, to the very maximum extent possible, or fully, before sealing and, again, from the compartments between seals 52 and 45, before sealing, so that they are hollow, but not air filled.

In the event that the cells of the crown and headband are filled with one-shot materials, wider filler openings must be provided at 30e, f and g. This is accomplished simply by merely limiting the heat seals surrounding such. In this case, granular ammonium nitrate (if cooling is desired) is first inserted into the cells when they are in proper orientation for filling, then a water bag thereafter. After removal of air from the cells, heat sealing across the filler openings may be effected. With respect to cells 49 and 50, when they are upwards, either as first filled or second filled, the granular ammonium nitrate is added through passages 58 and 59, then the water bags and, after rqmoval of air from the filled cells, the seal 52 is first made. Then, after clearing the air from the compartments above seal 52, seal 45 may be made. Using suitable machinery and procedure, seals 52 and 45 may be made simultaneously, with air removal from all noted portions. Also, air removal and opening sealing and trimming may be effected simultaneously with respect to the headband portion cells, given proper machinery.

DIMENSIONS

The following typical and optimum dimensions are given with respect to the previously described blank and filled scalp heat exchanging device. While the dimensions given are not absolutely critical, they are, indeed, optimum, functional for the purpose described and commercial. The length of headband 30 is preferably substantially 29 and ½ inches in blank, with its width 5 inches. The length of the crown section in the blank, from seal 48 to rear edge 45, may be 12¾ inches. The width of the crown rear end tab or filler channel portion may be slightly less than 7 inches. The width of the crown portion 44 at its front end next attachment 48 (inboard of the seals defining the tabs 53a and 53b) is about 11 and ½ inches. Each of the tabs 53 and 54 are about 3 and ¾ inches long and they range in width from 1 and ½ inch to a maximum of 2 and ½ inches at the inboard portions of tabs 53a and b. The length of strip 40 may be about 10 inches on the cell 35 and 4 and ½ inches therebeyond. The length of strip 42 is about 9 and ½ inches. The full length of tab or strip 38 is approximately 7 and ½ inches.

APPLICATION OF SCALP HEAT EXCHANGER

To apply the device to a patient, assuming rerefrigerable fluid fills the cells (and/or reheatable such), it must be refrigerated or heated to the proper temperature, depending upon whether the heat exchange is heating or cooling. Should the temperature effectable material or heat exchanging system comprise rupturable bags of liquid and dry mixing exothermic or endothermic reacting chemical, the device first must be activated. For the purposes of initial description, a cooling function would be assumed (for the primary object of the subject device, specifically, use with chemotherapy patients) and, as well, a reuseable fill in the cells of the device.

Assuming the latter and that the device is at the temperature or cooling or heating level optimum and desired, application may be effected in a number of different ways to achieve effective results. One such way will be described. It is preferably to have at least two people to aid assembly of the device, including the patient. A physically able individual, however, may apply the device themselves. With a physically incapacitated patient, two aides may be required for application.

In the case of a completely physically able person, the crown portion of the device is laid on top of the subject's head to basically support the crown portion with the lower portion at 48 above the patient's forehead. Then, grasping the end portions of cells 35 and 37 of headband portion 30, the patient may effect connection of the releasably engageable material 39 on strip 38 with the equivalent on the outside surface of cell 37, specifically strip 42 and material 43. This engagement may easily be made with the patient's hands behind his/her head with a tightening and slight compression of the headband portion around the head. Once this is done, then the patient, grasping the rear headband with one hand and the crown rear tab closely adjacent end 45 with the other, may engage the releasably securable material 62 and 63 on strips or patches 60 and 61 with equivalent material on strip 40 at 41. This adjustment is made in a manner that pulls the crown portion cells against the top of the patient's head, as well as centering over the head and enabling such to extend downwardly on each side of the crown thereof.

At this point, the side closures may be effected with the releasably engageable material 41 and 43 on strips 40 and 41 laterally of the patient's head, the engaging strips (on tabs 55 and 56) being pulled downwardly, outwardly and forwardly and/or rearwardly to make sure the entire scalp area is overlaid by the cells of the device including those in the headband portion and crown portion. Maximum and even scalp contact are both to be achieved by abutting crown and headband cells.

When an assistant is present, as is preferably the case, the assistant can be used to hold the crown portion free of the patient's head while a headband connection is made and then effect the crown connections, the back first, then the sides in order. If the patient is unable to contribute at all, two assistants may effect the mounting and application of the device to the patient's head with one holding the crown section free, the other making the headband connection, then the two of them completing the crown connections at the rear of the headband and at the sides thereof. Optionally, after the device is on the patient's head, the assembled cap may be overwrapped with an elastic bandage, stretching it slightly in order to hold the cap securely on the patient's head, providing additional compression thereon, such bandage being fastenable with a clip or tape.

In the event the device employs single use or one-shot chemical materials ((such as, for cooling use), granular ammonium nitrate and water segregated therefrom by a separate bag or the like in the cells), the device must be activated before applied. In such case, it would be laid down flat on the flat upper surface of the table or the like in the manner of the showing of FIG. 4. The operator then, one by one, presses down on the water bags or bag in each individual cell with the heel of one hand to activate (burst) them. Once this has been done, the previously described steps of application to the patient's head would be in order.

With respect to the stages of application, reference first may be made to FIG. 4. This is the outer surface of the device as it is laid on a table before application is to be made to the patient's head. In FIG. 13, the device is shown with the crown portion being held in substantially vertical position with the sides and free ends of the headband portion being brought around for connection together, as previously described, to provide a continuous headband before the rest of the assembly is effected. Looking at FIG. 14, this essentially gives the position of the device as it would be on a patient's head with the rear end portion of the crown and the rear portions of the cells thereof uplifted to display the rear headband connection. Two of the side tabs are shown down against and engaged with the headband by the Velcro or removably engageable material, which generally would not be the case in first assembly. The view of FIG. 14 does show the continuous headband circle made and its end attachments, as well as how the crown tabs come down to engage the strips on the side faces of the headband free end cells.

When the headband encirclement has been made (or is being made) it is most important, at this juncture, that the user or aide adjust the height of the headband and its position around the head of the subject at the desired level in front, at the sides, and in the back. This includes essentially an entire forehead overlap, an ear overlap and the bottom part of the skull overlap at the rear. (At this juncture, it may be mentioned, that, typically, plastic insulating sleeves (not seen) may be slipped over the subject's ears to protect them from excessive chill, if needed or desired.)

FIG. 7 shows a three-quarter perspective view, from the front, of the subject with the completed heat exchanging device on the subject's head. The cap device there comprises a unit held together by: (1) the headband to headband end connection, (2) the crown section rear flap to headband connection and (3) the crown side tabs to headband outer side connections. Given this basic assembly, the unitary device can be adjusted to finer precision and comfort for the user/wearer by manipulation of the side tabs and their engagement with respect to one another and the engaging strips of the side panels of the headband. Full hair area contact, as well as full forehead contact is preferably achieved, with the usual exceptions of the hair zones on the upper neck and very lowermost skull portion of the user. As noted, the application and use of a further compacting resilient bandage may give additional compression, particularly in the headband zone, if desired.

Thus it may be seen that substantially entire head or head top heat exchange, as well as overall head contact and compaction or compression and headband constriction, may be achieved in adjustable fashion for each individual user and patient.

INTEGRATED DEVICE DESCRIPTION

The subject heat exchanging headpiece for cooling or heating the entire or substantially the entire scalp (hair bearing) area of the human head comprises, in combination:

(1) An elongate, substantially rectangular headband portion 30 which is adapted to continuously and circumferentially wrap around the intermediate upper portion of a human head, including the forehead, the temple-ear head side zones and the lower back portion of the cranial vault.

(2) Means are provided, engageable between the free ends of the headband portion 30, which are adapted to secure the headband free end portions 30c and 30d together, one against the other, closely adjacent one another or overlapping one another, to form a normally continuous and optionally (but preferably) compressive or constrictive headband. This tension is fully adjustable by the essentially infinite adjustment possible between the strips and tabs 38, 39 and 42, 43.

(3) The headband portion most preferably comprises three, substantially equal volume hollow bags or cells of sealed, liquid-tight construction, the individual bags filled with temperature effectable or heat exchanging materials for repeatable or reuseable or, alternatively, single shot or single use application.

(4) A crown portion for the head piece is provided having a forward edge 48 secured essentially to the central portion of headband 30 at the top edge of cell 36. Crown portion 44 preferably comprises at least two elongate hollow bags of sealed, liquid-tight construction. Each such bag or cell 49 and 50 is filled with temperature effectable or heat exchanging materials for reuseable or single use applications.

(5) Means are provided at the rear edge or end of crown portion 44, such as the tab having rear edge 45, which are adapted to secure the crown portion rear end to a portion of the headband substantially 180° away from and opposed to the crown portion forward edge securement to the headband portion at 48. The specific parts of this means here shown are the Velcro or other equivalent material patches 60 and 61 which releasably engage with strip 40 and material 41 thereon.

(6) Means are provided for securing the side edges of the crown portion against or to the side upper edges of the headband free cells or end cells 35 and 37, that is, against the upper edges thereof at 30b. Such means involve the tabs 53 and 54 with the removably engageable patches thereon 55 and 56 which releasably engage with materials 41 and 43 on strips 40 and 42.

It thus may be seen that, when the free ends of the headband portion 30 are secured together, the rear tab or end of the crown portion 44 is secured to the headband portion and the side tabs 53 and 54 on the crown are also secured to the headband sides, a continuous, scalp contacting head piece for substantially completely and uniformly heat exchanging the hair bearing area or zone of the human scalp is provided. It is feasible to form the headband portion of two elongate cells or a single elongate cell, particularly in the case of single use heat exchanging materials or single shot such. In the two cell situation, the seam between the inboard ends of the cells will necessarily be centrally of the headband.

The optimum form of the headband for reuseable or repeatable application involves the presence of three individual cells in the headband, as at 35–37, inclusive, such of substantially equal size and volume or, if of different volume, the outer cells preferably equal volume and inner cell different volume. The center cell 36 preferably is at least the width of the headband-crown connection, or substantially that, to the crown portion, as seen at 48. A single cell or two cells in the headband is best in single use applications, the former seen in Truelock et al, supra.

In the crown, optionally, the entire crown cell portion may be but a single cell. However, this is preferably not the case and the most optimum form is that seen, specifically, parallel, preferably equal volume cells or bags 49 and 50 having a single central seam 51 at right angles to connection 48 therebetween. The tabs on the crown section are preferably spaced substantially as indicated, that is, the front pair of tabs 53a and 54b positioned substantially at the front edge of the crown section, while the rearward tabs 54a and 54b are positioned about intermediate the length of side edges 46, 47 from the rear termini of tabs 53 to seal 52. It should be noted that, at the front edges of tabs 53, the connection, to the headband portion, of the front part of the crown at 48, is lesser length than the full width of cells 49 and 50 thereat. This permits small portions of those cells to lie downwardly past the headband with respect to the patient's head and this construction is preferable. Such serves to fill in the coverage at the corners and provide full heat exchange for the front portion of the head.

GENERAL REMARKS

According to the best available records, some 75 million chemotherapy doses were given in the United States of America in 1979. This number has been increasing, from year to year.

It is not commercially or medically practical to employ a chin-tie or under-the-chin tie in order to maintain a device of the character described cinched on or tightly applied to the subject's head. The reason for this is because of the unfortunate real possibility of vomiting problems occuring during the actual chemotherapy process.

With the subject device, it has become (as opposed to the earlier Truelock et al, supra, device) possible for a physically able subject or patient to apply this device without the cooperation of a helper, aide or nurse. It is, of course, easier to apply it with help. In any case, any reasonably able patient can certainly readily and perfectly apply the device with but a single aide or helper. A single aide or helper can apply the device to a helpless patient in some circumstances, but, in general, under conditions of this sort, two aides are best.

Optionally, the subject device may employ surfaces of non-allergenic sulfide paper laminating to polyethylene. The purpose of the use of such paper or surfacing in hospital products is to minimize water condensation. Thus, condensation on the patient's head, hospital gown, any towels used or sheets, if the patient is in bed, would be minimized.

The most optimum times of application of this device can be described as follows. The device should be fitted to the scalp in cooled or chilled condition (cooled for cancer chemotherapy) and left in place at least 10 minutes prior to the I.V. chemotherapy drug injection. The device is, of course, left in place during the entire effective time of action of the drug, which is typically a minimum of 40 minutes after completion of drug administration. The 28° F. operating temperature of an efficiently used water-ammonium nitrate pack (of the sort used in a single shot application) will produce good results. Temperature control is critical with a nonself limiting device. It must not be cool or heated to the point where discomfort, frostbite or burning of the patient takes place.

With respect to results, the positive effects recited in the Beam et al article are, at the least, to be expected to be achieved. At the very worst (under the most rigorous conditions of chemotherapy to a given patient, depending on the patient's condition and the intensity and frequency of chemotherapy dosing), the subject device will minimize hair loss.

By employing a rerefrigerable or reheatable compound, the subject device becomes reuseable. This approach, as noted, may raise certain problems, including excessive chilling or heating. To some extent, some hospitals do not prefer the use of reuseable devices. While to a certain extent this may be because of convenience of billing procedures to the patient, additionally, device cleaning and cross contaimination problems, between patients, as well as storage, must be considered. The optimum manner for a reuseable device to be employed is for single patient utilization. Additionally, the provision of refrigeration devices or heating devices reasonably adjacent to application points must be considered with the use of this construction.

It has been discovered that the presence of seams 33 and 34 do not substantially reduce the effective use of the heat exchange in the hatband or headband area, particularly when constriction is employed. When an elastic bandage is additionally employed over the headband, with slight stretch thereof and additional compression, such holiday areas at the seams are further minimized because of compaction of the cells with respect to one another. The contact or overlap of the cells at the rear end of the headband avoids holidays in this zone. It is most important to have full, continuous heat exchange of the forehead zone because of the numerous blood vessels passing therethrough. This is one reason for having the center cell 36 present in a multicell construction of the headband.

There should be a minimum area of "holidays" in the applied heating or cooling cap. This is first established by having all the cells (headband and crown portions alike) so full that, in the applied cap, with constriction and compression, substantially full coverage of the hair growing area of the head (scalp) can be obtained and, yet, substantially continuous abutment of one cell with respect to the other can be accomplished. Secondly, this is accomplished by constricting the headband cells upon the head in encirclement thereof and overlapping or contacting the free end headband cells. Further, pulling the rear ends and sides of the crown portion top cells down into contact with the headband cells in assembly stops edge holidays. Finally, an additional overlie of elastic bandage in constriction, after the side edges of the crown cells have been brought into contact with the side top edges of the headband cells by use of the tabs 53 and 54, is further effective.

The subject device, as noted, has two or more head size adjustments. The first of these effected is the hatband or headband adjustment in the headband portion, per se. This is a complete circle of compression on all blood vessels leading into the scalp. The second adjustment is the crown size. This is obtained, after the headband is closed, by pulling the rear of the crown portion far enough back to fairly tightly compress the crown cells on the patient's head when the rear crown connection to the 180 degree opposed headband portion is made. The third adjustment is made at the sides of the crown of the device with the tabs engaging against the side faces of the headband end cells. This involves a lateral compression of the crown cells following the longitudinal such.

In the event that the engagements called out, that is, the removably engageable attachments, involve a Velcro type attachment, where one face of such attachment is essentially loops and the other face of such attachment is essentially hooks, then, typically, the loop portions would be found in the attachments 41 and 43 on strips 40 and 42. Hook attachments, then, would be on patches 60, 61 and tab attachments 56a and b and 55a and 55b, as well as interior strip 38 and the material 39 thereon. The zones noted may be reversed in the hook/loop presentation. The point is that strips 38, 55a, 55b, 56a, 56b, 60 and 61 all attach onto one or both of strips 40 and 42.

The subject device is not useful in leukemia, because of the circulating cancer cells in the blood.

It is important to realize that, while it is desirable to have some pressure in all zones of the heat exchanging device, in contact on the head, and particularly in the headband for limited constriction of the vessels going into the head, one definitely wants to avoid the creation of a tourniquet effect which can result in pain, fainting, psychological effects and possible damage to some blood vessels.

With respect to the reuseable, freezer-type cells, if a temperature of minus ten degrees F. is inadvertently reached, frostbite will result. This means it is necessary to both carefully control the freezer temperature (if such were to be used in a hospital or clinic) and, as well, test the heat exchanging device temperature before application. The noted minimum temperature of ammonium nitrate-water combination does not give frostbite. If such mixture were used, it would typically be 50% ammonium nitrate and 50% water by weight. With respect to ammonium nitrate-water packs, the ambient temperature at which the devices are stored relate to the water heat when activated and thus the ultimate temperature reachable.

FIGS. 15-17, Inclusive

Referring to FIGS. 15-17, inclusive, therein is shown a variation of the subject construction wherein the useable or repeated use option with respect to the preferred embodiment previously described is abandoned. That is, instead of having rechillable or reheatable temperature effectable material for heat exchange in the headband portion cell or cells and crown portion cell or cells, such is replaced by heat exchanging chemicals which are effective only upon mixing and activation thereof. In the case of chilling or cooling, the preferred mix is granular ammonium nitrate and water. In the time honored form of use of such (going back, at least, to the Robbins et al U.S. Pat. No. 2,925,719, issued Feb. 23, 1960 for "Refrigerating Package", as well as Caillouette, U.S. Pat. No. 3,643,665, issued Feb. 22, 1972 for "Therapeutic Pack For Thermal Applications"), the dry granular chemicals and a rupturable bag of water are provided within a compartment or cell effective for cooling or heating upon rupturing of the bag of water by compression through the wall of the compartment or cell when ready for use.

Aside from the change in the materials received in the headband portion and crown portion of the device, the primary change (which is optional but preferred) in the device when liquid cellular heat exchanging materials are employed lies in the provision of the headband portion being made up of but of a single cell. In this manner, the filling of the headband cell portion with the water bags and granular material is simplified (filling may be made from one or both ends of the headband portion) and, as well, when the device is activated and the water mixes with the granular material, the headband portion then acts as a truly continuous band around the head without any problem of holidays or gaps in heat exchange at the seams between the cells. While a single cell may be employed in the head band portion with the reuseable materials, such is definitely not preferred because of the tendency of a chilled gel-like material to aggregate in zones of less pressure or tension around the head and also not uniformly adapt to circumferential contact and engagement as is the case with a more fluid substance like water. Accordingly, although individual cells may be provided in the headband portion of the one shot or nonreuseable type device, with an individual water bag and granular chemical provided in each cell, such is definitely not preferred.

In the construction of FIGS. 15-17, inclusive, then, parts which are exactly or substantially the same as parts in the previously described figures are numbered the same, but primed. Such parts will not be redescribed in detail. The description of the structure of these parts is here incorporated by reference from the previous parts of this specification.

Turning to the distinctive structure of FIGS. 15-17, inclusive, in the headband portion 30', there is but a single cell 100 which, when filled and sealed, contains one or more rupturable water bags 101 and 102, as well as a quantity of granular ammonium nitrate or other reactive chemical 103. In assembly of the device, if, for filling, but one end, say 33', is left unsealed for filling, a first water bag 102 may be inserted and pushed to the other end of the head band portion 30', a quantity of ammonium nitrate charged and then the second water bag 101. Use of one or more liquid or water bags in the cell is optional with the size of the bag being proportioned to the number used and the quantity of ammonium nitrate or other heat exchanging chemical employed therewith. Alternatively, a first charge of ammonium nitrate is inserted in the head band portion 30', then the water bag, then a second charge of ammonium nitrate.

Referring to the crown portion 44, the cells 49' and 50' each have a liquid or water bag 104 and 105 inserted therein from the free end filler openings as previously described with respect to filling of the reuseable chemical. Quantities of ammonium nitrate 106 (seen only with respect to cell 50') are also charged (or other heat exchanging chemical) and the reactive elements of the endothermic or exothermic mixture sealed within the respective cells by the seams 48', 51' and 52', the last being applied after filling and the former being provided before filling.

It additionally should be mentioned that, after the head band 30' portion cell is filled, as well as each of the cells 49' and 50' of the crown portion, before the final heat seals are applied, air is expelled, as far as possible, from the cells before the sealing thereof. This is to enable readily feasible bursting (by compression) of the liquid or water bags 101, 102, 104 and 105 and, additionally, permit effective fitting and shaping of the cells and application of the device to the patient's head (not hindered by air bubbles).

Typical quantities of water and ammonium nitrate in the headband portion 30' would be 650 grams of water in 325 gram bag packages before rupture and 650 grams of ammonium nitrate. In each of the crown section cells, a 225 gram water bag may be matched with 225 grams of ammonium nitrate.

To apply the device of FIGS. 15–17, inclusive to a patient, the device first is activated. The device may be laid down flat on the flat upper surface of a table in a manner of illustration of FIG. 15 (or with the device inverted). The operator then, one by one, presses down on the water bags with the heel of one hand to activate (burst) them. After activation of each of the cells, the manner of application of the device to the patient's head is precisely as described with respect to the reuseable device of the previous figures. Accordingly, such will not be redescribed in detail.

The point of the assembly application, as previously described, is to provide not only controlled constriction around the entire head band portion (as well as cooling from the head band into the constrictive zone), but also at least some compaction on the entire top of the head from the completed cap with the cells of the head band and crown section pressed, one against the other and held down against the patient's head. Thus entire head heat exchange, as well as at least some over all head compaction or compression and head band constriction are all achieved in adjustable fashion for each individual user patient.

The subject device, in both its reuseable and nonreuseable forms, possesses many advantages over the use of ice, per se. Patient comfort, pliability, convenience, sustained cooling and uniform surface cooling are all advantages achieved by the subject developments. The efficient action of these devices aids in reducing the physical, psychological and social trauma of expected hair loss in chemotherapy treatments. The subject devices are pliable, relatively lightweight and may be fitted without undue stress to the patient. Each of the devices mold conveniently to the specific size and shape of the patient's head and scalp. When applied immediately after freezing activation or treatment in the case of the reuseable device or chemical activation in the case of the one-shot heat exchanger, cold treatment may be provided for up to 90 minutes, depending upon ambient temperatures. Made of suitable materials, the reuseable device has a virtually unlimited useful product life span under normal use and service.

FIG. 21

In FIG. 21 there is shown an ear protector of convenient and effective form which may be employed to avoid discomfort and earache from prolonged application of cooling or heating heat exchange to the scalp of a patient. The device is generally designated 110 and typically comprises a pair of formed pieces or segments of insulating foam plastic 111 and 112 which are heat sealed together at the edge peripheries thereof as at 113. The inboard (next to the patient's head) sheet or segment is vertically and arcuately relieved in a door or window portion 114 thereof centrally of the lower edge 111a and opening out of the same. This relief enables the ear cover 110 to be fitted down over the patient's earlobe from above and gives complete coverage and protection to each ear and heat or cold insulation of effective protection.

FIGS. 18–20, Inclusive

In previous description of the application of the device to the patient's or user's head, stages of application have been previously described. FIG. 18 shows the crown portion of the heat exchanging head piece being snugged down on the top of the patient's head, with the rear portion of the crown being pushed into engagement with the outside surface of already made engagement of the ends of the headband portion. Thus, the engagement of FIG. 10 is in the process of being made after the stage of FIG. 14. This is a joining of the Velcro or like material portions 63 and 62 on the insides or undersides of tab portions 59 and 58, respectively, with the Velcro or like portions 41 of the elongate strip 40 which is overlying and in engagement (through side 39 thereof) with the like Velcro strip 43 on cell 37. As may be seen in FIG. 14, cells 35 and 37 are in substantial end abutment with one another by virtue of the noted tabs 39 and 43 being in positive engagement, thus to create a circumferential headband in essentially continuous contact with the lower portion of the patient's scalp and preferably in slight construction or compression thereon.

Once the engagement is made as in FIG. 18, then the tabs (54a and 53a as seen in FIGS. 18 and 53b and 54b in other view) are pulled both laterally and downwardly on each side of the head to the desired position and adjustment for engagement with the Velcro portions 41 on the left side of the head (FIG. 9) and 43 on the right hand side of the head (FIGS. 10 and 18). These engagements are also seen in FIG. 12, which is the underside view of the assembled cap. It should be noted that any initial engagements for mounting the head piece on the patient may be redone and adjusted as desired for optimum fit and full contact, as well as proper headband portion compression and constriction and crown portion contact and compression down on the scalp. Said otherwise, once the headband portion has been tightened and secured into correct position and desired constriction and compression by successive attachments as required, then the crown portion may be attached, adjusted and fixed with respect thereto by means of successive engagements of the rear tab portion on the crown and the side tabs thereof, in order to have comfortable yet full contact and pressurized engagement with the entire scalp area of the patient, all without discomfort.

Once the full, proper mounting of the head piece on the patient's head by virtue of the Velcro engagements of the headband portion ends to one another and the crown portion rear and side tabs to the headband portion Velcro external bands, then, optionally, but preferably, a final application of elastic bandage, wrapping same circumferentially around the headband portion, may be made. The elastic bandage is of conventional type, generally designated at 115 and is of a length sufficient to wrap circumferentially several times around the patient's head. If necessary, the inner free end of the bandage may be taped by adhesive tape to the outer surface of the head piece. The width of the bandage is preferably sufficient to slightly exceed the height of the assembled device (FIGS. 9 and 10, as well as FIG. 7) on the patient's head. In this manner, the upper and lower edges of the elastic bandage, by virtue of the elasticity thereof, curl in around and somewhat under the lower edge of the headband portion and over and inward of the upper edge of the headband portion and crown portion outer edges so as to give more than just peripheral coverage. This may be seen in FIGS. 19 and 20. Preferably, a minimum of three wraps of bandage over the device are employed and the free end 115a remaining at the ends of the wrap may be secured by adhesive tape members 116 temporarily to the body of the bandage to hold such.

The purpose of this wrap is multi-fold. In the first place, heat or cooling loss from the heat exchange cells of the device is minimized during application of the device. Secondly, additional compaction and constriction, to the degree desired and to make most effective the headband portion compression and constriction may be applied. This makes it less necessary that the precise desired constriction and compression be entirely achieved with the Velcro or like material attachment. It also, by making more sure of the adjustment of the device on the head of the patient, permits greater freedom of movement of the patient's head during the time of chemotherapy.

The subject device has been found to offer chemotherapy patients safe, comfortable application of cold therapy to the scalp. Scalp hypothermia has been proven effective in the prevention of hair loss among patients receiving Doxorubicin. Thus, additionally, see Anderson, J. E. et al "Prevention Of Doxorubicin-Induced Alopecia By Scalp Cooling In Patients With Advanced Breast Cancer" British Medical Journal 282: 423-424, 1981.

From the foregoing, it will be seen that this invention is one well adapted to attain all of the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

We claim:

1. A heat exchanging head piece for repeatedly cooling or heating substantially the entire scalp (hair bearing) area of the human head, comprising, in combination:

(1) an elongate, substantially rectangular head band portion adapted to be continuously and circumferentially wrapped around the human head, including the forehead, the temple-ear head side zones and the lower back portion of the cranial vault, said head band portion having substantially parallel, spaced apart, opposed upper and lower edges and end edges, the latter positioned substantially at right angles to the former, said head band portion also having inner and outer faces with respect to the head of the user, as well as two free ends at the extremities thereof, said head band portion including three elongate, axially series aligned, hollow cells of sealed, liquid tight construction, said cells each containing temperature affectable materials for heat exchange, one of said cells positioned in symmetrical opposition to the crown portion and being at least substantially the width thereof, the other two cells outboard of said first described cell being of substantially equal length to one another and each such being at least substantially free of any connection to the said crown portion, (2) a crown portion for such head piece having a forward end and edge secured centrally to the substantial center of the upper edge of the head band portion, side edges extending rearwardly from the said forward edge securement and a free rear end and edge spaced rearwardly from and substantially parallel to said forward edge thereof, said crown portion also having inner and outer faces with respect to the head of the user, said crown portion including two elongate, hollow cells of sealed, liquid-tight construction of substantially equal size and substantially congruent form, said cells each containing temperature effectable materials for heat exchange, said cells extending substantially parallel to one another and substantially at right angles to the forward connection of the crown portion to the head band portion, (3) means releasably and repeatably engageable between the free ends of the said head band portion adapted to releasably and repeatably secure said free ends together, at least in close adjacency to one another, in adjustable head band size fashion, to form a continuous head band around the head of a human subject, said means for securing the head portion end edges together comprising a first elongate length of removably engageable material fixed to the outer face of one end of said head band portions and a second elongate length of removably engageable material fixed in a portion of the length thereof to the inside face of the other end of said head band portion, with a further portion of the latter length thereof extending beyond said end, said first and second lengths removably engageable, one with the other, (4) said head band portion being at least sufficiently long that the end edges thereof will at least substantially abut one another, when said head band portion is continuously and circumferentially wrapped around a human head, (5) measn adjacent the rear end of said crown portion, on the inner face thereof, adapted to releasably and repeatably secure the crown portion rear end to the outer face of said head band portion substantially 180° away from and opposed to the crown portion forward edge securement to the head band portion, in adjustable crown size fashion, the said means at the rear end edge for the crown portion comprising a rearward tab extension of the crown portion of sufficient length and width that such extension is able to overlie, contact and engage a portion of the outer end face of each of the free end portions of the head band portion after the latter have been removably secured to one another, the underside of said crown portion rearward tab extension and a portion of the outer end face of each of the head band end portions having means thereon for releasably engaging, one with the other, (6) the width of said crown portion cells adjacent the connection of the crown portion to the head band portion being greater than the width of the center cell of the head band portion, and the width of said crown portion cells in the portions thereof spaced farthest away from the head band-crown connection being equal to a substantial portion of the width of the center cell of the head band portion, said crown portion cells not extending into said crown portion rearward tab extension, the front connection of said crown portion to said head band portion being substantially the width of the center head band portion cell and in registry therewith, (7) means for releasably and repeatably securing the side edges of the crown portion to opposed outer side faces of the head band portion, whereby to form, when: (a) the free ends of the head band portions are releasably secured together, (b) the rearward tab extension of the crown portion is releasably secured to the ends of the head band portion and (c) the side edges of the crown portion are releasably secured to the side faces of the head band portion, a reuseable, size adjustable, substantially continuous contact, scalp contacting head piece for substantially completely and uniformly heat exchanging substantially the entire hair bearing zone of the human scalp, the means for securing the side edges of the crown portion to the opposed outer side faces of the head band portion comprising, first, two depending tabs on each of the side edges of the crown portion, said tabs each having removable engaging means on the inner faces thereof and being fixed at one end thereof to a side edge of the crown portion, one of said two tabs depending from the forward side edge of each respective crown portion edge and the other of said tabs depending from each said crown portion side edge at a position substantially intermediate the forward and rearward edges thereof and, second, lengths of removable engaging means fixed to the opposed outer side faces of the head band portion in the entire length of the outer cells thereof, the said depending tabs each being individually adapted to be releasably and adjustably engaged to a chosen portion of one of the outer side faces of the head band portion by the releasable engaging means thereon.

2. A heat exchanging head piece as in claim 1 wherein the temperature affectable material in both the head band portion cells and crown portion cells comprises a fluidic chemical substance which is repeatably refrigerable for repeated cooling purposes and also repeatedly heatable for repeated heating purposes.

3. A heat exchanging head piece as in claim 1 wherein the temperature affectable material in the head band portion cells and crown portion cells comprises a fluidic chemical substances which is repeatably refrigerable for repeated cooling purposes.

4. A heat exchanging head piece as in claim 1 wherein the temperature affectable material in the head band portion cells and crown portion cells comprises a fluidic chemical substance which is repeatably heatable for repeated heating purposes.

* * * * *